United States Patent
Faries, Jr. et al.

(10) Patent No.: US 7,744,640 B1
(45) Date of Patent: Jun. 29, 2010

(54) THERMAL TREATMENT GARMENT AND METHOD OF THERMALLY TREATING BODY PORTIONS

(75) Inventors: Durward I. Faries, Jr., Las Vegas, NV (US); Bruce R. Heymann, Vienna, VA (US); David Hendrix, Ashburn, VA (US)

(73) Assignee: Medical Products, Inc., Chantilly, VA (US)

( * ) Notice: Subject to any disclaimer, the term of this patent is extended or adjusted under 35 U.S.C. 154(b) by 128 days.

(21) Appl. No.: 11/130,416

(22) Filed: May 17, 2005

Related U.S. Application Data

(63) Continuation-in-part of application No. 10/413,565, filed on Apr. 15, 2003, now Pat. No. 6,927,316, which is a continuation-in-part of application No. 09/635,919, filed on Aug. 10, 2000, now Pat. No. 6,548,728.

(60) Provisional application No. 60/148,271, filed on Aug. 11, 1999.

(51) Int. Cl.
*A61F 7/00* (2006.01)
(52) U.S. Cl. .................. 607/109; 607/96; 607/108; 607/112
(58) Field of Classification Search .............. 607/96, 607/108–112, 104
See application file for complete search history.

(56) References Cited

U.S. PATENT DOCUMENTS

| | | | |
|---|---|---|---|
| 683,991 A * | 10/1901 | Rowe | .................. 607/110 |
| 1,000,750 A | 8/1911 | Nerli | |
| 2,069,643 A | 3/1936 | Burke | |
| 2,653,601 A | 11/1950 | Morrison | |
| 3,279,465 A | 10/1966 | Cherio et al. | |
| 3,343,537 A | 9/1967 | Graham | |
| 3,463,161 A * | 8/1969 | Andrassy | .................. 607/110 |
| 3,521,632 A | 7/1970 | Graham | |
| 4,147,921 A * | 4/1979 | Walter et al. | .............. 219/211 |
| 4,403,653 A * | 9/1983 | Davidson | .................. 165/170 |
| 4,661,099 A | 4/1987 | Von Bittera et al. | |
| 4,671,267 A | 6/1987 | Stout | |
| 4,699,146 A | 10/1987 | Sieverding | |
| 4,909,244 A | 3/1990 | Quarfoot et al. | |
| 4,991,574 A | 2/1991 | Pocknell | |
| 5,005,567 A | 4/1991 | Gilman et al. | |
| 5,038,779 A | 8/1991 | Barry et al. | |
| 5,115,801 A | 5/1992 | Cartmell et al. | |
| 5,156,601 A | 10/1992 | Lorenz et al. | |
| 5,204,110 A | 4/1993 | Cartmell et al. | |

(Continued)

*Primary Examiner*—Roy D Gibson
*Assistant Examiner*—Kaitlyn E Helling
(74) *Attorney, Agent, or Firm*—Edell, Shapiro & Finnan LLC

(57) ABSTRACT

A thermal treatment garment of the present invention includes an outer structure layer, an interior lining formed of a gel material that directly contacts a body portion of a user when the garment is worn by the user and a thermal treatment layer to thermally treat and control temperature of the garment. The thermal treatment layer heats and/or cools the gel material to a selected temperature or selected temperature range and is controlled by a controller. In an exemplary embodiment, the garment includes a cap to thermally treat the user's head, where the structure layer has a generally convex outer surface and the interior surface of the gel layer is generally concave and contoured to engage with and at least partially envelop at least one selected portion of the user's head.

32 Claims, 8 Drawing Sheets

U.S. PATENT DOCUMENTS

| | | | |
|---|---|---|---|
| 5,292,347 A * | 3/1994 | Pompei | 607/104 |
| 5,328,449 A | 7/1994 | Andrews et al. | |
| 5,425,702 A | 6/1995 | Carn et al. | |
| 5,527,270 A | 6/1996 | Chase et al. | |
| 5,643,189 A | 7/1997 | Masini | |
| 5,662,624 A | 9/1997 | Sundstrom et al. | |
| 5,682,617 A | 11/1997 | Tumas | |
| 5,800,490 A | 9/1998 | Patz et al. | |
| 5,935,595 A | 8/1999 | Steen | |
| 5,968,003 A | 10/1999 | Sisson | |
| 6,071,304 A | 6/2000 | Augustine et al. | |
| 6,095,992 A * | 8/2000 | Augustine | 602/2 |
| 6,156,059 A * | 12/2000 | Olofsson | 607/109 |
| 6,277,143 B1 * | 8/2001 | Klatz et al. | 607/104 |
| 6,416,534 B1 | 7/2002 | Montagnino et al. | |
| 6,589,270 B2 | 7/2003 | Augustine | |
| 6,927,316 B1 * | 8/2005 | Faries et al. | 602/43 |
| 2002/0026226 A1 | 2/2002 | Ein | |
| 2004/0138729 A1 | 7/2004 | Ladmer | |

* cited by examiner

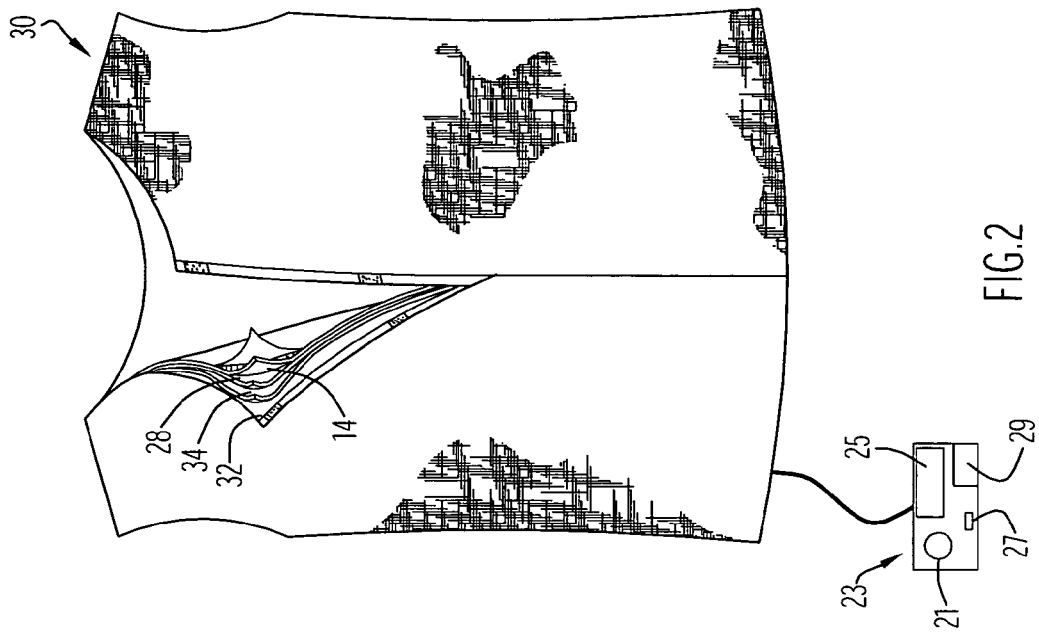
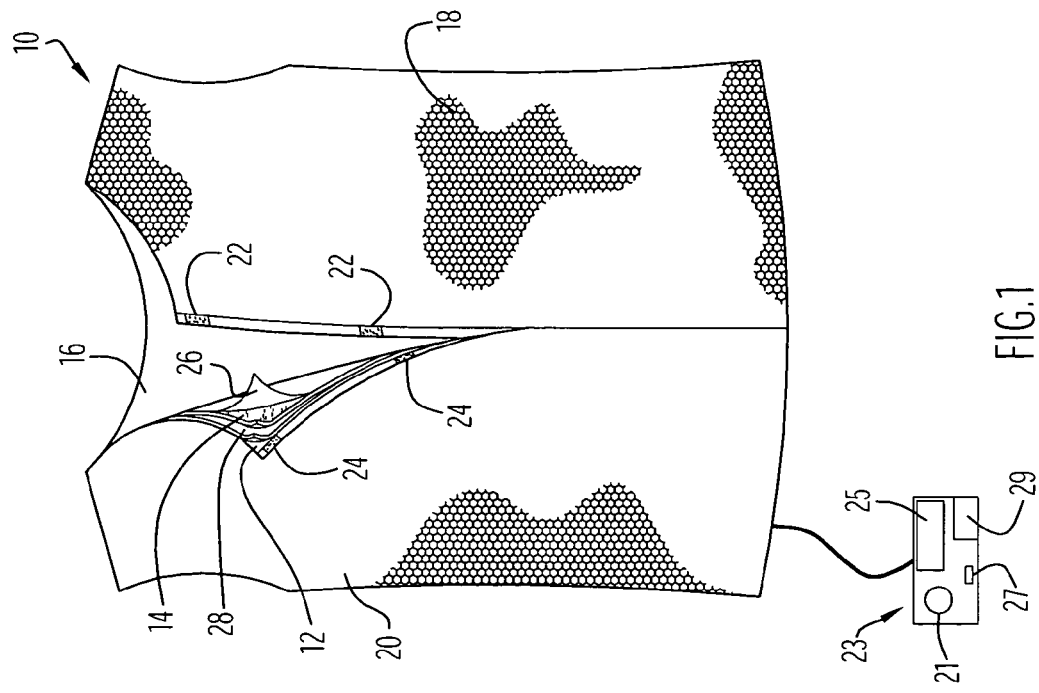

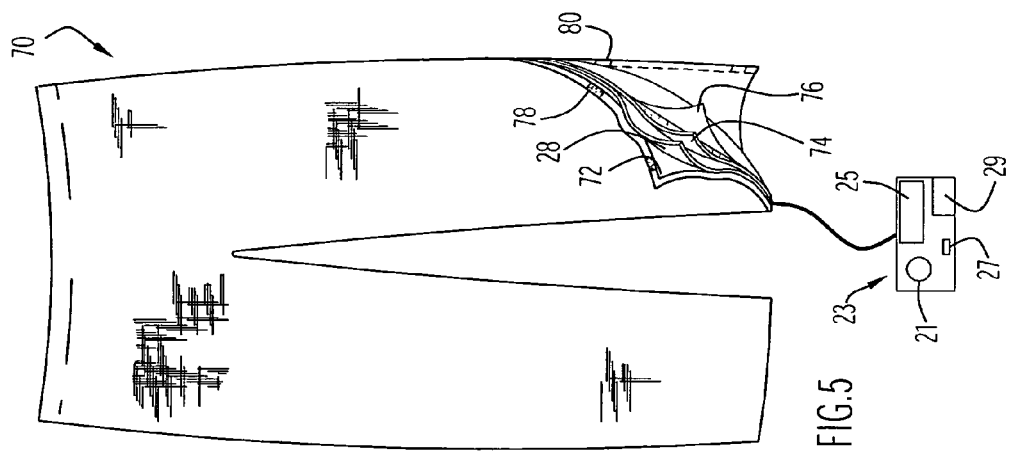
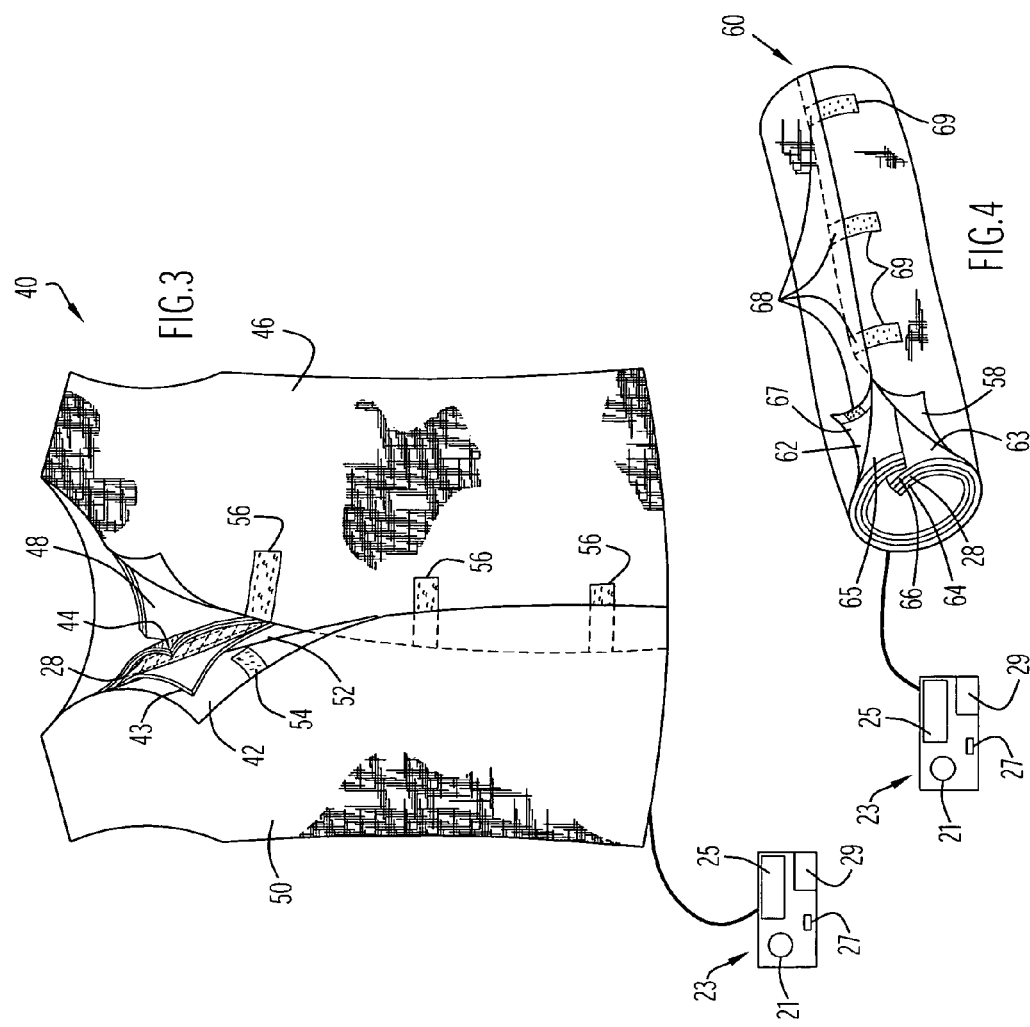

THERMAL TREATMENT GARMENT AND METHOD OF THERMALLY TREATING BODY PORTIONS

CROSS-REFERENCE TO RELATED APPLICATIONS

This application is a Continuation-in-Part of U.S. patent application Ser. No. 10/413,565, entitled "Thermal Treatment Garment and Method of Thermally Treating Body Portions" and filed Apr. 15, 2003, now U.S. Pat. No. 6,927,316, which is a Continuation-in-Part of U.S. patent application Ser. No. 09/635,919, entitled "Wound Dressing Garment" and filed Aug. 10, 2000, now U.S. Pat. No. 6,548,728, which claims priority from U.S. Provisional Patent Application Ser. No. 60/148,271, entitled "Wound Dressing Garment" and filed Aug. 11, 1999. The disclosures of the above-identified patent applications are incorporated herein by reference in their entireties.

BACKGROUND OF THE INVENTION

1. Field of the Invention

The present invention relates to a garment shaped to conform to the contours of and thermally treat body parts and, more particularly, to a garment lined with a thermal element and a self-adhesive sheet-like gel layer forming a garment inner surface to directly contact and thermally treat the skin and/or a wound.

2. Description of the Related Art

Various gel-like materials are known to have properties that promote the healing of wounds such as severe burns. Sheet-like wound dressings having a self-adhesive layer formed of a gel material have been used to treat skin wounds by placing the gel material in direct contact with the wound. These dressings are secured to the wound via adhesion of the gel material to healthy skin surrounding the wound. The gel materials are typically tacky to the touch and readily adhere to the skin, but are easily removed from the skin without significantly pulling the skin or disturbing or clinging to newly formed tissue at the wound site, and leave no perceptible residue. These gel materials tend to manage fluids seeping from the wound in a manner conducive to healing and can be used to deliver additives, such as anti-microbial agents, to the tissue of the wound to prevent infection. In effect, such gel layers operate to seal the wound and function as a synthetic skin.

For example, U.S. Pat. No. 4,661,099 to von Bittera et al., incorporated herein by reference in its entirety, discloses a self-adhesive sheet-like structure having a support layer and an adhesive polyurethane gel layer which adheres to the skin and leaves virtually no residue when removed. The sheet-like structure can be used as a wound dressing in which a gauze bandage is held in place on the wound by the polyurethane gel layer that adheres to the skin surrounding the wound. On dry wounds or wounds having only slight discharge, the polyurethane gel layer can be adapted for use in direct contact with the wound by chemically altering the gel to increase its absorbency.

U.S. Pat. No. 5,115,801 to Cartmell et al., incorporated herein by reference in its entirety, discloses a multi-layer burn dressing having a hydrogel material layer that is placed in direct contact with the burn site on the skin. The hydrogel serves as a bio-compatible, bacterial protective, fluid absorbing, cushioned skin-like medium that facilitates the healing process.

Silicone gel sheets have also been applied directly to damaged skin to treat burns and scars, as disclosed, for example, in U.S. Pat. No. 4,991,574 to Pocknell, incorporated herein by reference in its entirety. In particular, silicone gels have been found to prevent keloid and hypertrophic scarring at wound sites and to reduce the visibility of existing scars. Such silicone gels are manufactured, for example, by Applied Silicon Corporation.

The aforementioned gel dressings are universally produced in flat sheets, with the gel material layer typically being secured to at least a substrate layer providing structural integrity to the dressing. One problem with such dressings is that, while these flat sheets are generally pliable and can be molded to a degree to conform to skin contours, such flat sheets have a limited ability to cover highly contoured skin surfaces of the body (e.g., the face, the scalp, the neck, the shoulders, the hands, the complete torso and/or upper body and arm(s), the complete lower body and/or leg(s), bent elbows and knees, hips, ankles, and feet). Consequently, these sheet-like dressings are generally most suitable for covering only a limited skin area. Further, due to their sheet-like shape, these dressings cannot generally form a secured enclosure to envelop a body part and therefore must rely almost exclusively on the adhesion of the gel material to remain secured to the body.

To cover highly contoured portions of the body, it would be necessary to cut pieces of the sheet dressing to suitable sizes and shapes, and to cover the wound in sections with plural dressing pieces. The set of individual dressing pieces might imperfectly cover the wound, and the cutting and application of customized dressing pieces would be time consuming and would make rapid application of the dressing virtually impossible. Further, this cumbersome operation would have to be performed each time the dressing is changed.

Burn dressings that are shaped to conform to certain portions of the body have long been known in the field. These dressings typically employ conventional wound-contact materials that are absorbent and permeable to fluid and air, such as gauze and fabric. For example, U.S. Pat. No. 3,343,537 to Graham, incorporated herein by reference in its entirety, discloses burn dressings for covering various anatomical parts. The dressings consist of a porous, multi-layer silk lining which comes into contact with the wound, and a multi-layer gauze backing.

U.S. Pat. No. 3,279,465 to Cherio et al., incorporated herein by reference in its entirety, discloses a bandage in the form of a vest having two short sleeves. The bandage consists of a net-like material that holds gauze in place over the wound.

U.S. Pat. No. 5,328,449 to Andrews et al., incorporated herein by reference in its entirety, discloses a wound dressing in the shape of a glove having a porous skin-contacting layer, an absorbent intermediate layer, and an outer layer formed of a water-proof breathable material.

While both gel materials and dressing garments have been used for many years in the treatment of burns and other wounds, to date, no known attempts have been made to develop a dressing garment that employs a skin-contacting gel material. This may be due in part to the fact that sheet-like, gel-based dressings are rather thick, heavy and awkward in comparison to the thin, lightweight, fabric-like materials conventionally used to form dressing garments, and the appearance and gummy, resilient feel of such bulky gel-based dressing sheets do not readily suggest the fashioning of garments from these dressings. The fact that sheet-like, gel-based dressings are conventionally applied via adhesion to a limited skin area, rather than as an enclosure that surrounds or drapes over a body part, further contributes to the perception that sheet-like, gel-based dressings do not lend themselves to use in garments and that these dressings may be ill-suited and impractical for such applications.

Moreover, sheet-like, gel-based dressings are functionally unrelated to conventional burn garments. Sheet-like, gel-based dressings are substantially impermeable to air and moisture, and have limited or no absorbency. The gel material is designed to essentially seal the wound and functions substantially as a synthetic layer of skin over the wound, preventing any external interaction. In contrast, conventional burn garments are formed of permeable, absorbent materials that remove and absorb fluids exuded from the wound. Unlike a synthetic skin, such garments function more as a separate, external covering that rests over the wound and encourages healing of the wound by permitting a controlled flow of air to the wound and a controlled removal of fluid from the wound.

These structural and functional differences between sheet-like, gel-based dressings and conventional burn garments would explain, at least in part, why these wound treatments have existed side-by-side in the field for years without any consideration of possible applications of gel materials in garment-like dressings.

In addition, the healing process and user comfort may be enhanced by warming the gel material (e.g., to temperatures at or near body temperature) and applying the warmed gel material to the skin or wound. However, the above-described related art devices do not provide a manner to thermally treat and control temperature of the gel material, thereby limiting the healing potential of the garments and/or dressings and providing a level of discomfort to the user.

OBJECTS AND SUMMARY OF THE INVENTION

Accordingly, it is an object of the present invention to provide a garment designed to include a thermal element and surround or drape over a highly-contoured body part, such as the head of a patient, to thermally treat garment gel material in direct contact with skin located on the body part(s).

It is another object of the present invention to reduce the time required to apply a dressing to a highly contoured portion of the body (e.g., the patient's head) and to avoid the need to form a customized dressing at the time the dressing is to be applied to the wound.

Yet another object of the present invention is to provide a thermal treatment garment that is adjustable in size to fit a portion of the body for bodies in a range of sizes.

Still another object of the present invention is to rely on the combination of adhesion and conformance to body shape to secure a garment to the skin of a user.

The aforesaid objects are achieved individually and/or in combination, and it is not intended that the present invention be construed as requiring two or more of the objects to be combined unless expressly required by the claims attached hereto.

According to the present invention, a thermal treatment device for thermally treating a portion of a user's body includes a garment comprising a structure layer having an inner surface that faces toward the user when the garment is worn by the user, a gel layer coupled to the inner surface of the structure layer and forming an interior surface of the garment that engages with at least one selected portion of the user's body, and a thermal treatment material coupled with the gel layer and configured to thermally treat the gel layer and the user.

In an exemplary embodiment, the garment comprises a cap to thermally treat the user's head, where the structure layer has a generally convex outer surface and the interior surface of the gel layer is generally concave and contoured to engage with and at least partially envelop at least one selected portion of the user's head.

The device may also include a controller to control the thermal treatment material so as to thermally treat the gel layer and the user to a selected temperature or within a selected temperature range.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 1 is front view in elevation of a thermal treatment garment for a human torso in accordance with an exemplary embodiment of the present invention.

FIG. 2 is a front view in elevation of a thermal treatment garment for a human torso in accordance with another embodiment of the present invention.

FIG. 3 is front view in elevation of an adjustable thermal treatment garment for a human torso in accordance with another embodiment of the present invention.

FIG. 4 is a perspective view of an adjustable thermal treatment garment for a human arm in accordance with another embodiment of the present invention.

FIG. 5 is a front view in elevation of a thermal treatment garment for the lower body in accordance with another embodiment of the present invention.

DETAILED DESCRIPTION OF THE PREFERRED EMBODIMENTS

Figure 6A:
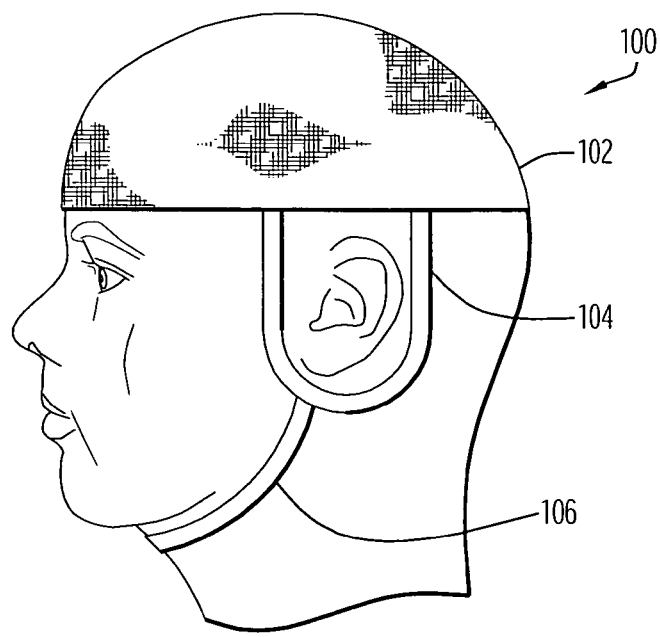
FIG. 6A is a side view in elevation of an adjustable thermal garment in the form of a cap as worn by a user, for covering portions of a human head in accordance with another embodiment of the present invention.

A thermal treatment garment in accordance with an exemplary embodiment of the present invention for thermally treating skin or wounds (e.g., burns, scars, etc.) is illustrated in FIG. 1. The garment includes a thermal element to heat or cool the garment to a desired temperature as described below.

The garment may be utilized for treatment of wounds, such as burns or scars, or may be employed to heat or cool user body portions (e.g., warm users in cold weather or environments and/or during skiing or other cold weather activities, cool users in hot weather or environments or during activities leading to perspiration, etc.). Specifically, the exemplary garment takes the form of a sleeveless vest 10 that is shaped and sized to envelop the torso of the human body. As used herein, the term "envelop" means to substantially cover by enclosing, encasing, surrounding or fitting over a portion of the body, such that the correspondence between the shape of the garment and the covered portion of the body generally contributes to keeping the garment secured on the portion of the body. It will be understood that the term "envelop" does not require that an entire body part be covered; thus, for example, a portion of an arm can be enveloped while another portion of the arm or the hand can remain uncovered. It will be further understood that, while the garment of the present invention is configured to envelop a portion or all of a body part or plural body parts, the garment may include one or more openings for adjacent body parts (e.g., a torso garment may include openings for the waist, neck and arms, and a glove-like garment may include an opening for the arm). Thus, as used herein, the term "partial enclosure" refers to an enclosure that has at least one opening through which a body part adjacent a site can extend.

Exemplary garment 10 includes an outer structure layer 12 formed of a pliable material, an inner lining gel layer 14 formed of a self-adhesive, sheet-like gel material suitable for contacting skin or treating wounds (e.g., severe burns or scars) and a thermal treatment layer 28 typically disposed between the structure and gel layers. In the embodiment shown in FIG. 1, structure layer 12 is formed of a mesh fabric made of nylon or the like. Structure layer 12 provides the overall shape of the garment and provides a framework for supporting gel layer 14. Structure layer 12 of sleeveless vest garment 10 includes three mesh fabric panels sewn together at their edges. Specifically, garment 10 includes a back panel 16 sewn along part of one side edge and part of the top edge to a front left panel 18 (e.g., the left panel with respect to a wearer as viewed in FIG. 1), and along part of another side edge and part of the top edge to a front right panel 20 (e.g., the right panel with respect to a wearer as viewed in FIG. 1), leaving arm and neck openings between the panels. The edges of the panels that are sewn together have complementary shapes forming seams that correspond to contours of the portion of the body over which the seams of the garment fit (in this case, the shoulders and the sides of the torso).

In addition to providing the shape and framework of the garment, structure layer 12 supplements gel layer 14 in securing the garment to the portion of the body (in this example, the torso). Specifically, front left and right panels 18 and 20 meet, but are not permanently attached, along a vertical (as worn on the body) centerline extending from the front center of the neck opening to the bottom of the garment at the front center of the waistline. Front left and right panels 18 and 20 are detachably securable to each other along the front vertical centerline with a fastener. The fastener can be any one or a combination of conventional fastening mechanisms, including, but not limited to: hook and loop fasteners, buckles, buttons, clasp or clipping mechanisms, snaps, straps with locking rings, zippers, string or fabric ties, straps or frictional force.

By way of example, exemplary garment 10 shown in FIG. 1 includes complementary hook and loop fasteners 22 and 24 respectively attached to the corresponding edges of the left and right front panels of structure layer 12. Fasteners 22 and 24 engage each other to secure together the left and right front panels 18 and 20 along the front vertical centerline of garment 10. By securing the open edges of structure layer 12 with fasteners, structure layer 12 forms a partial enclosure that augments the gel layer in keeping the garment securely attached to the body. Further, the detachability of the left and right front panels 18 and 20 allows sleeveless vest garment 10 to be placed over and secured to the torso with a minimum of movement of the torso and garment 10 and with a minimum of contact between the torso and gel layer 14 of garment 10 prior to correctly positioning garment 10 on the torso.

As used herein and in the claims, the term "securable" is used broadly to describe both edge portions that are permanently secured to each other and edge portions that are detachably securable (e.g., with fasteners). As will be understood from the foregoing description, structure layer 12 of garment 10 includes edges that are permanently secured to each other along seams as well as edges that are detachably securable to each other with fasteners. However, as will be evident from other embodiments described and shown herein, the present invention is not limited to embodiments of garments having both permanently secured edges and detachably securable edges.

While shown in FIG. 1 as a nylon mesh fabric, the structure layer of the present invention is not limited to any particular material or combination of materials. The structure layer can comprise one or more layers formed of one or more materials, including, but not limited to: woven fabrics and textiles formed of natural and/or synthetic materials, non-woven fabrics and textiles formed of natural and/or synthetic materials, and elastomeric materials.

Self-adhesive, sheet-like gel layer 14 serves as an interior lining of garment 10 and is coupled to an inner surface of the garment to cover at least a substantial portion thereof, such that gel layer 14 presents an interior surface for directly contacting the skin of the wearer. Gel layer 14 can be described as a soft, tacky, non-friable gel sheet that readily adheres to skin and that leaves no perceptible residue (e.g., no sticky or gummy residue) on the skin when removed. While described as sheet-like, it will be understood that the gel layer need not be planar, and may be curved or arcuate in one or more dimensions as required to conform to the shape of the garment. The gel material is slightly adhesive to skin, but does not tend to significantly disturb newly formed tissue at a wound site when removed. The gel material essentially functions as a synthetic skin over a wound, allowing the wound to heal with a minimum of interaction with the external environment.

The gel material of gel layer 14 can be, for example a semi-occlusive silicone gel, such as a silicone gel manufactured, for example, by Applied Silicon Corporation. Such silicone gels have been used in the treatment of burns and scars. Specifically, silicone gel sheeting has been found to improve wound healing, reduce pain, and produce a better cosmetic resulting by flattening and softening hypertrophic and keloid scar tissue and returning the skin to its natural color. However, any other suitable gel materials may be utilized (e.g., hydrogels, polyurethane gels, etc.). Further, the gel material is beneficial to skin to assist with dry skin or cracking, corns, bunions, scarring and other skin disorders. Optionally, additives (e.g., anti-microbial agents, Aloe, Vitamin E or other vitamins, medicaments, lotions, ointments, etc.) can be incorporated or infused in the gel material to enhance the skin and/or prevent infection of a wound. In this case, the gel material further serves as an osmotic absorption or semi-permeable membrane to enable the additives to directly enter the skin or wound.

By way of non-limiting example, gel layer 14 can be approximately one-eighth to one-sixteenth of an inch in thickness or approximately one to five millimeters in thickness. It is to be understood that these dimensions are provided by way of example only and are not in any way limiting on the scope of the invention. Gel layer 14 can be secured to the interior surface of the garment in a variety of ways. In the exemplary embodiment shown in FIG. 1, gel layer 14 directly contacts and is secured to thermal treatment layer 28, at least in part, by the inherent self-adhesiveness of the gel material. The bond between structure layer 12, gel layer 14 and thermal treatment layer 28 can be formed by any one or a combination of: pressure (e.g., pressing the layers together), heat, and a suitable adhesive. The gel layer sheeting and thermal treatment layer can be bonded to the panels of the structure layer prior to securing the panels together, or the panels of structure layer 12 can be secured together prior to lining the garment with gel layer 14 and thermal treatment layer 28. In either case, gel layer 14 can comprise a plurality of sheets shaped and sized to line the desired portion of the garment. As explained in greater detail below, to provide maximum utility, the sheet or sheets of gel layer 14 preferably cover substantially all of the interior of the garment, with gel layer 14 being separable or peelable from the garment so that selected portions of gel layer 14 can be removed when not required to cover a particular body portion or wound.

Prior to application to the skin, gel layer 14 is covered with a protective thin, peelable layer 26, such as a plastic film, to prevent gel layer 14 from accidentally contacting other surfaces. In operation, peelable layer 26 is peeled off of gel layer 14 just before applying the gel layer to the skin of the wearer.

Thermal treatment layer 28 is disposed between structure layer 12 and gel layer 14 as described above. The thermal treatment layer may be of any shape or size and is typically dimensioned to substantially cover gel layer 14. The thermal treatment layer may be secured or fastened to the structure and/or gel layers via any conventional or other techniques (e.g., sewing, adhesives, the gel layer adhesiveness, etc.). Alternatively, the thermal treatment layer may be placed in or on the garment or garment layers at any suitable locations (e.g., on the garment exterior, between the structure and gel layers, between plural gel layers, in direct contact with the skin, etc.). Thermal treatment layer 28 thermally treats and controls the temperature of gel layer 14. The gel layer basically serves as a thermal conductor to distribute thermal energy from the thermal treatment layer to a wearer in a substantially uniform manner.

The thermal treatment layer generally heats the garment and may be implemented by a conventional etched foil silicon rubber heating pad. Alternatively, heating wires or coils may be secured to or disposed within a suitable housing or structure (e.g., plastic layer, pad or platform mounting the coils or wires, etc.) to form thermal treatment layer 28. The garment may be utilized to warm wearers in cold environments or to assist healing by heating the gel material covering a wound as described above. Further, the garment heating may assist with circulatory problems and/or dissolving blood clots in any body portions or extremities. A controller 23 is coupled to and controls thermal treatment layer 28 to heat the garment to a desired temperature.

A temperature sensor (not shown) is disposed within the garment to provide a temperature indication to controller 23. The temperature sensor may be disposed proximate the wearer or the thermal treatment, structure or gel layers and may be implemented by any conventional or other temperature sensor (e.g., RTD, infrared, etc.) to provide a temperature indication (e.g., of the structure, gel or thermal treatment layers, wearer, etc.). The controller utilizes the temperature indication to control the thermal treatment layer accordingly to heat the garment to a desired temperature. In particular, the controller controls power to the thermal treatment layer. If the temperature indication from the temperature sensor is equal to or exceeds a desired or user-specified temperature, controller 23 disables power to thermal treatment layer 28. When the temperature indication from the temperature sensor is less than the desired temperature, the controller enables power to the thermal treatment layer.

Controller 23 may be implemented by any conventional or other microprocessor, controller and/or circuitry. The controller includes a power switch 21, display 25, controls or input devices 27 and a power source 29. Power switch 21 is a conventional switch to control power to the controller, while power source 29 is typically implemented by batteries in order to enable the controller to be transportable with garment 10. Display 25 may be implemented by any conventional or other display (e.g., LCD, LED, etc.) and displays the measured and/or desired temperatures and other information (e.g., time, date, etc.). Input devices 27 (e.g., buttons, keys, etc.) enable entry of a desired temperature and other information by a user and facilitate control of display 25 to display the actual and/or set point temperatures and other information.

The thermal treatment layer may alternatively be implemented by a thermoelectric device, such as a Peltier chip, to heat and cool the garment to a desired or user-specified temperature. The thermal treatment layer may include a housing or structure (e.g., pad or platform, etc.) with heat sinks coupled to the thermoelectric device to provide heating and cooling. The thermoelectric device basically enables one or more heat sinks to absorb thermal energy (e.g., thereby cooling the surrounding environment), while enabling one or more other heat sinks to expel thermal energy (e.g., thereby heating the surrounding environment) based on the direction of current or voltage polarity applied to the device. The heat sinks are basically dispersed throughout the thermal treatment layer and disposed proximate the wearer, or the structure or gel layers as described above. Controller 23 controls the polarity and/or distribution of power to the thermoelectric device to control heating and cooling of the garment by the heat sinks to the desired temperature. In particular, the temperature sensor provides a temperature indication to controller 23 as described above. If the temperature indication from the temperature sensor is equal to or exceeds a desired or user-specified temperature, controller 23 provides a particular polarity to the thermoelectric device to enable the heat sinks to cool the garment. When the temperature indication from the temperature sensor is less than the desired temperature, the controller provides an opposing polarity to the thermoelectric device to enable the heat sinks to heat the garment. The thermoelectric device may be configured to only heat or cool the garment, where the controller may control (e.g., enable or disable) power to the device accordingly to attain a desired garment temperature. The garment heating and cooling may be utilized to assist healing or warm or cool wearers in various environments or during activities (e.g., workouts, at the beach, etc.). Further, the garment may serve as a hot or cold compress to treat various wounds, bruises and muscle injuries (e.g., pulls, strains, sprains, swelling or inflammation, etc).

The thermal treatment layer may further be embedded within the garment structure and/or gel layers. For example, the heating pad or wires may be disposed within the structure and/or gel layers to heat the garment. Similarly, the heat sinks may be disposed within the structure and/or gel layers to heat and cool the garment.

In operation, vest 10 is placed on a wearer with gel layer 14 in contact with the skin or wound. The wearer enables power to controller 23 via power switch 21 and enters a desired temperature into the controller through input devices 27. The controller controls the polarity and/or distribution of power to the thermal treatment layer in response to a temperature indication from the temperature sensor to attain a desired garment temperature as described above. The gel material may include or be infused with various types of medicaments to assist with wounds or skin conditions as described above. When the session is completed, the wearer disables power to the controller via power switch 21 and removes vest 10.

Referring to FIG. 2, a thermal treatment garment 30 in accordance with another embodiment of the present invention includes a structure layer 32, gel layer 14 and thermal treatment layer 28. The structure, gel and thermal treatment layers are substantially similar to the layers described above. Structure layer 32 is formed of a fabric material and is coupled to thermal treatment layer 28 via an intervening layer 34. Intervening layer 34 can be, for example, a galvanized or ungalvanized elastomeric material to which the thermal treatment and/or gel layers readily adhere. The gel and thermal treatment layers reside on one side of intervening layer 34, while structure layer 32 is disposed on the other side of intervening layer 34. The thermal treatment and structure layers may be permanently or removably attached to the intervening layer via any conventional or other techniques (e.g., sewing, adhesives, the gel material adhesiveness, etc.). In addition to serving as a base layer to which structure layer 32, thermal treatment layer 28 and/or gel layer 14 can be readily attached, intervening layer 34 also provides additional overall strength to the gel sheeting without significantly reducing the flexibility of the gel sheeting. The thermal treatment layer is coupled to and controlled by controller 23 to thermally treat garment 30 to a desired temperature in accordance with a temperature sensor measurement in substantially the same manner described above. The temperature sensor may be disposed within the garment at any location (e.g., proximate the wearer or the gel, structure, intervening or thermal treatment layers, etc.).

It will be readily understood that other structure layer configurations fall within the scope of the invention. For example, the structure layer can comprise any number of layers, or the structure layer can be formed of a single elastomeric layer without any fabric layers. In accordance with another embodiment, the structure layer is formed using a molding technique, wherein the structure layer comprises a material shaped by setting in a mold.

Where the structure layer includes a plurality of panels permanently secured to each other along seams (see FIGS. 1-3 and 5), the panels of the structure layer can be secured along the seams by sewing, stitching, staples or any other suitable mechanism. For example, where the panels of the structure layer comprise an elastomeric or thermoplastic material, the panels can be secured at their edges by heat fusing.

In accordance with another embodiment of the present invention, a thermal treatment garment is adjustable in size to snugly fit body parts in a range of sizes. Referring to FIG. 3, an adjustable thermal treatment garment 40 for the torso includes a structure layer 42, an intervening elastomeric layer 43, an inner gel layer 44 and a thermal treatment layer 28. The layers and arrangement are similar to those shown in FIG. 2, except that thermal treatment layer 28, intervening elastomeric layer 43 and gel layer 44 are detached or detachable from structure layer 42 at least in the vicinity of the edges of the structure layer that are securable with fasteners. Specifically, a front left panel 46 (e.g., the left panel with respect to a wearer as viewed in FIG. 3) of structure layer 42 is detached from edge portion 48 of underlying thermal treatment, intervening and gel layers 28, 43 and 44 along the entire vertical edge of the front left panel over a distance of at least an inch, and preferably at least two inches, in the horizontal direction. Similarly, a front right panel 50 (e.g., the right panel with respect to a wearer as viewed in FIG. 3) of structure layer 42 is detached from edge portion 52 of underlying thermal treatment, intervening and gel layers 28, 43 and 44 along the entire vertical edge of the front right panel over a distance of at least an inch, and preferably at least two inches, in the horizontal direction. As seen in FIG. 3, edge portions 48 and 52 are essentially flaps in the shape of vertical strips extending along the front vertical centerline of garment 40 in parallel with edges of structure layer 42. The overall size of the garment is selected to be at least as large as necessary to cover the torso of a wearer, such that, when gel layer 44 is smoothly attached to the skin of the torso, left and right edge portions 48 and 52 overlap along the front vertical centerline of the garment. For example, right edge portion 52 of the thermal treatment, intervening and gel layers overlaps and extends over left edge portion 48, but extends underneath left front panel 46 of structure layer 42. Gel layer 44 of the overlying right edge portion readily adheres to left edge portion 48 of underlying intervening layer 43, thereby snugly sealing gel layer 44 to the torso (alternatively, the overlapping portion of the edge portion can be trimmed off).

The detached portions of left and right front panels 46 and 50 of structure layer 42 also form overlapping flaps. In the foregoing example, the edge portion (flap) of right front panel 50 overlaps and extends over the edge portion of left front panel 46. A set of adjustable fasteners 54 and 56 respectively attached to left and right front panels 46 and 50 are used to secure the edge portions of the front panels to each other in the overlapped position. By way of non-limiting example, fasteners 54 and 56 can be complementary hook and loop fasteners. To account for variation in the degree of overlap, the fasteners of at least one of the sets of fasteners 54 and 56 extend longitudinally in the horizontal direction (i.e., transversely of the garment body) to permit engagement of the fasteners over a range of overlap positions. In the preferred embodiment, the fasteners are rectangular. Adjustable length straps or any other type of adjustable position fasteners can be used with adjustable garment 40.

The adjustability of the garment permits a wide range of body sizes to be fit with a limited number of different-sized garments (e.g., small, medium, large, extra large). The thermal treatment layer is coupled to and controlled by controller 23 to thermally treat garment 40 to a desired temperature in accordance with temperature sensor measurements in substantially the same manner described above.

As will be understood from the foregoing, an important aspect of the adjustable garment of this embodiment of the present invention is the region of detachment between the outer structure layer and the inner gel layer in the vicinity of the edges of the structure layer that are secured via fasteners. This detachment region permits the gel layer and the structure layer to be independently overlapped and independently secured to provide a superior fit. Specifically, the overlapping portion of the gel layer can slide underneath the opposing edge of the structure layer and adhere directly to the opposing (overlapped) gel layer (or the elastomeric backing of the gel layer), thermal treatment layer or intervening layer. That is, a first gel layer edge portion can be interleaved between a second, opposing gel layer edge portion and a second, opposing structure layer, with a second structure layer edge portion being interleaved between a first intervening layer edge portion and its corresponding first structure layer. Further, the two edges of the structure layer can be overlapped and fastened to each other without interference from the other garment layers (e.g., gel, thermal treatment and/or intervening layers), thereby permitting a simple fastener design.

While described as having both left and right detached layer flaps, it will be understood that a similar result can be obtained by forming a detached layer flap along only one of the left and right edges of the front panels. In this case, independent overlapping is achieved by extending a first structure layer edge portion and its attached first layer edge portion between a second intervening layer edge portion and a second structure layer edge portion that has been separated from the second intervening layer edge portion.

The gel layer can be permanently detached (i.e., separated) from the structure, intervening and/or thermal treatment layers in the edge region, or the gel layer can be detachable from the structure, intervening and/or thermal treatment layers in the edge region (as used herein and in the claims, the term "separable" is used broadly to describe both permanently detached edge portions and detachable edge portions or layers). Specifically, outer structure layer 42 can be peelable from intervening layer 43 at least in the vicinity of the front vertical centerline edges of garment 40. Preferably, a significant degree of tugging force is required to tug or peel apart structure layer 42 and intervening layer 43 so that these layers are not readily susceptible to being unintentionally detached.

Optionally, the structure layer can be detachable over its entire inner surface from the thermal treatment and gel layers (or an intervening layer). If a particular wound does not require a gel layer over the entire extent of the garment, this detachability feature allows portions of the thermal treatment and/or gel layers to be selectively removed to improve the comfort of the garment, while the entire structure layer remains intact to provide complete support for the gel and thermal treatment layers and to preserve the ability of the structure layer to secure the garment to the body. In this case, the thermal treatment layer may be formed of a plurality of thermal units that are controlled by the controller in the manner described above to thermally treat the garment. The thermal units may be detached from the vest and controller. Alternatively, the thermal treatment layer may remain intact to thermally treat a wearer after detachment of gel layer portions.

According to another embodiment of the adjustable garment, the structure and gel layers are not detached, and one edge of the garment overlaps and extends over the other edge of the garment, and adjustable fasteners, such as straps, secure the exterior of the garment. While this embodiment may be simpler in some respects, the overlapping portion of the gel layer may have only limited adhesion to the underlying structure layer, and the design of the adjustable fasteners may be limited by absence of a structure layer flap detached from the gel layer.

While the garment of the present invention has been shown in FIGS. 1-3 as a sleeveless vest for covering the torso, it will be understood that the present invention includes garments or other articles that cover any portion of the body, including, but not limited to, any one, combination, or portion of the following body parts: fingers, hands, wrists, elbows, shoulders, arms, the head, the scalp, the face and individual facial features, the neck, the breasts, the torso, the back, the waist, hips, the groin or genitals, legs, knees, ankles, feet, and toes. Thus, the garment of the present invention may take a number of different forms, including, but not limited to: a finger wrap, a glove, a mitt, head or wrist bands, a sleeve, a vest, a jacket or coat, a mask, a skull cap, a neck tube, a girdle, shorts, pants, leggings, a leg wrap, a sock, a toe wrap, a scarf, an undergarment, blanket (e.g., for babies, a quilt, etc.), bed sheet, etc.

Referring to FIG. 4, an adjustable thermal treatment garment in the form of a sleeve 60 for on an arm is shown. Sleeve 60 includes an outer structure layer 62, an intervening elastomeric layer 63, an inner gel layer 64 and thermal treatment layer 28. The structure, gel, intervening and thermal treatment layers and arrangement are similar to those described above. Structure layer 62 is formed of a pliable material, such as one or more of the above-described structure layer materials. Structure layer 62 comprises a single, generally rectangular panel which wraps around the arm, with longitudinal edges that meet or overlap along a line extending generally along the length of the arm. Structure layer 62 can also be formed from plural panels. Intervening elastomeric layer 63, gel layer 64 and thermal treatment layer 28 are detached or detachable from structure layer 62 at least in the vicinity of the longitudinal edges of structure layer 62. The thermal treatment layer is typically disposed between the gel and intervening layers and is coupled to and controlled by controller 23 to thermally treat the sleeve to a desired temperature in accordance with temperature sensor measurements in substantially the same manner described above.

Specifically, a first longitudinal edge portion 58 of structure layer 62 is detached from edge portion 66 of underlying intervening layer 63 and a second longitudinal edge portion 67 of structure layer 62 is detached from edge portion 65 of underlying intervening layer 63. Structure layer edge portions 58 and 67 overlap with intervening layer edges 65 and 66 in an interleaved manner, much like the edges portions of the vest garment shown in FIG. 3. Specifically, the second intervening layer edge portion 65 extends over first intervening layer edge portion 66 but beneath first structure layer edge portion 58 (i.e., between edge portions 66 and 58), and the first structure layer edge portion 58 extends over the second intervening layer edge portion 65 and beneath the second structure layer edge portion 67 (i.e., between edge portions 65 and 67).

Fasteners 68 and 69 are attached to the longitudinal edges of structure layer 62 to enable the longitudinal edges to be secured to each other in an overlapped manner. By way of non-limiting example, fasteners 68 and 69 can be complementary hook and loop fasteners. To account for variation in the degree of overlap, the fasteners of at least one of the sets of fasteners 68 and 69 have a rectangular shape, extending longitudinally in the horizontal direction to permit engagement of the fasteners over a range of overlap positions.

Sleeve 60 shown in FIG. 4 is an example of a garment of the present invention having a structure layer with edge portions detachably secured to each other with fasteners, but with no edges permanently secured to each other along seams. Other embodiments of the present invention may include a structure layer with only permanently secured edges and no detachably securable edges. For example, a glove or mitten (not shown) to be fitted over the hand can include an inner gel layer lining, an intermediate thermal treatment layer and an outer structure layer formed of two or more panels sewn together, with a single opening for the wrist/arm (with no edges detachably securable with fasteners).

Referring to FIG. 5, according to yet another embodiment of the present invention, a thermal treatment garment 70 in the form of leggings for covering skin or wounds below the waist and on the legs is shown. Leggings 70 include an outer structure layer 72 formed of a pliable material, an inner lining gel layer 74 formed of a self-adhesive, sheet-like gel material and thermal treatment layer 28 disposed between the gel and structure layers. The structure, thermal treatment and gel layers and arrangement are similar to those described above. Gel layer 74 is covered with a protective thin, peelable layer 76, such as a plastic film, to prevent gel layer 74 from accidentally contacting other surfaces prior to application to the wound. The thermal treatment layer is coupled to and controlled by controller 23 to thermally treat garment 70 to a desired temperature in accordance with temperature sensor measurements in substantially the same manner described above.

Structure layer 74 is formed of a number of panels that are seamed together in much the same way as conventional pants or trousers. However, to avoid the need to slide the leggings over the legs and hips, the leggings are preferably detachably securable along the outseam of each leg portion of leggings 70. For example, as shown in FIG. 5, the front left leg panel (e.g., the left leg panel with respect to a wearer as viewed in FIG. 5) is detachably securable to the back left leg panel along the left outseam with fasteners, such as complementary hook and loop fasteners 78 and 80 respectively attached to the corresponding edges of the front and back left leg panels. Although not explicitly shown in FIG. 5, the front and back right leg panels of leggings 70 (e.g., the right leg panel with respect to a wearer as viewed in FIG. 5) can also be detachably securable along the right outseam. If only a selected portion of the lower body is to be covered, unnecessary portions of the leggings can be removed or cut off from the portion applied to the skin or wound. For example, if only the left leg requires to be covered, gel layer 74 and/or thermal treatment layer 28 can be removed from leggings over all but the left leg portion of the leggings (leaving intact the structure layer), or the left leg portion of the leggings (the structure, gel and thermal treatment layers) can be completely detached from the rest of the leggings.

Figure 6B:
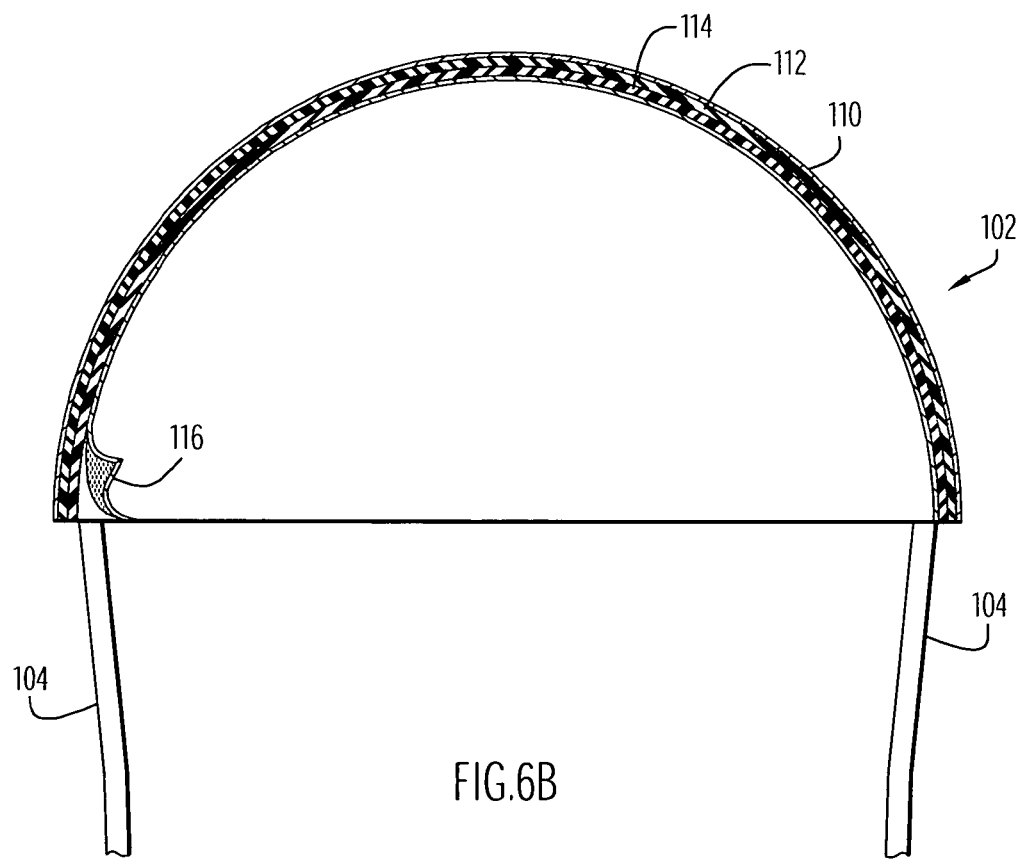
FIG. 6B is a partial front view in elevation and cross-section of the garment of FIG. 6A.

In accordance with another embodiment of the present invention, a thermal treatment garment is formed in the shape of a covering or cap to facilitate covering selected portions of a user's or patient's head. An exemplary embodiment of such a garment is depicted in FIGS. 6A and 6B. A thermal treatment garment 100 includes a rounded covering or cap 102 that forms a generally smooth and convex outer surface and a generally smooth and concave inner surface so as to generally conform with the contour of a human head. The cap is suitably dimensioned to be worn over at least the upper surface or crown of the head (as shown in FIG. 6A) so as to treat portions of the scalp and/or other head portions. The cap includes a pair of looping straps 104 extending from opposing lower end surfaces of the cap, where each strap is suitably aligned along the periphery of the cap and dimensioned to extend and form a generally U-shaped loop about an ear when the cap is worn by the user/patient.

A chin strap 106 extends between and is secured (or is securable) to the looping straps. The chin strap is suitably dimensioned to facilitate looping of the chin strap around neck and/or chin portions of the patient when cap 102 is worn on the patient's head. The chin strap can be constructed of any one or more suitable materials that permits releasable securing of the cap to the patient's head in a firm but comfortable manner. In an exemplary embodiment (as is depicted in FIGS. 6A and 6B), the chin strap is a single segment that is preferably constructed of an elastic material that can be stretched to fit around chin and/or neck portions of the user to firmly affix the cap to the user's head. Alternatively, the chin strap can include a single segment that is secured to one of the looping straps 104 and releasably securable to the other looping straps via any suitable complementary fasteners (e.g., hook and loop fasteners, snap or buckle fasteners, etc.). Further still, the chin strap can include two segments that are each secured to one of the looping straps 104 and are releasably securable to each other at any suitable locations along the segments and via any suitable complementary fasteners (such as the those described above) that are disposed on the segments. Thus, the chin strap provides an adjustability feature for firmly securing cap 102 to the head of different patients during different medical procedures or other applications.

Thermal treatment cap 102 includes a series of layers that are substantially similar to the various layers of the previously described thermal treatment garments depicted in FIGS. 1-5. Referring to FIG. 6B, cap 102 includes an outer structure layer 110, a gel layer 114 and a thermal treatment layer 112 disposed or sandwiched between the structure and gel layers. In addition, cap 102 preferably includes a peelable layer 116 disposed adjacent gel layer 114 and that is removable from the gel layer prior to applying the cap to the head of a patient. Each of the layers forming the cap can be of any suitable types and configurations as described above for the structure, gel, thermal treatment and peelable layers of the previous embodiments. Optionally, the cap may further include an intervening layer disposed between the gel and structure layers that is similar in type and configuration to the intervening layers of previously described embodiments of thermal treatment garments. It is to be noted that the outer structure layer of the thermal treatment cap is depicted in the figures as a woven fabric layer for exemplary purposes only, and the structure layer for the cap is not limited to such materials. In addition to the previously described types of materials of which the structure layer can be formed (e.g., nylon mesh, woven fabrics and textiles, elastomeric materials, etc.), the structure layer of the thermal treatment cap can also be constructed of any suitably rigid material (e.g., plastic materials and/or metal materials) so as to form a generally rigid outer shell to which the other layers of the cap are directly or indirectly secured, where the structure layer maintains a generally curved contour for all the layers that conforms to the patient's head.

The cap can further include detachable sections that facilitate removal of selected portions of the gel layer and/or thermal treatment layer over selected sections of the cap in a similar manner as described above in relation to the other embodiments (e.g., the thermal treatment garment of FIG. 3). As noted above, providing detachable gel layer and/or thermal treatment layer sections that are removable from the cap allows for selective removal of those sections from the cap in situations where such treatment is not necessary on the head of the patient (e.g., in instances where only portions of a patient's scalp need to be treated). Thus, a further adjustability feature is provided and improves the comfort for the wearer of the thermal treatment cap based upon different treatment applications.

Figure 6C:
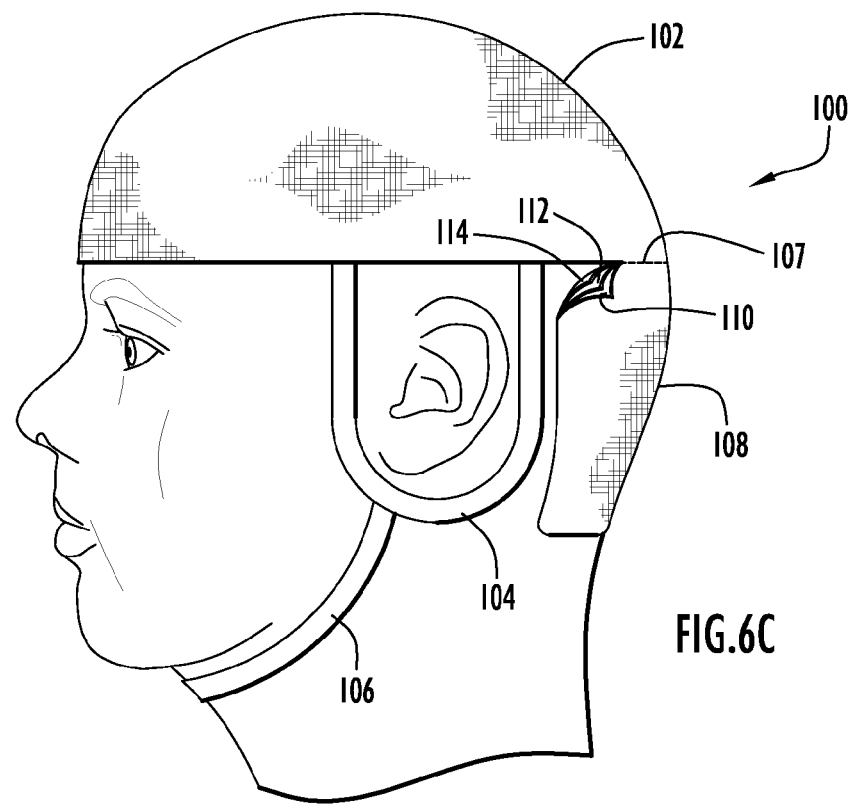
FIG. 6C is a side view in elevation of the garment of FIG. 6A as worn by a user including a rear dressing portion to cover additional surface areas of the head.

The thermal treatment cap can also be modified to include one or more additional wound dressing segments that extend downward from the cap to increase the overall contacting surface area between the cap and the user's head (e.g., portions of the head at or below ear level). The additional wound dressing segments preferably include at least a structure layer, thermal treatment layer, gel layer and peelable layer arranged in the same manner as described above for the cap. Referring to FIG. 6C, a wound dressing segment 108 is secured to and extends a selected distance transversely from the lower end of cap 102. The wound dressing segment is further suitably dimensioned to extend a selected distance with respect to the periphery of the cap. For example, the wound dressing segment can be dimensioned to cover a rear portion of the patients head that extends from the cap a selected distance between and below the ears. Additional wound dressing segments can also be secured at one or more other selected locations around the lower end of the cap. The wound dressing segments can further be detachable from the cap (e.g., via dashed line 107 depicted in FIG. 6C) to facilitate removal of selected sections and treatment of selected areas at and/or below the ear level and around the head of a patient.

The thermal treatment cap may also include additional adjustability features to render the cap suitable for use with a variety of different head sizes For example, the cap described above can be modified such that the outer structure layer includes two opposing ends (rather than being one continuous section as depicted in FIG. 6A), where one end of the structure layer can be overlapped with the other end a selected amount to selectively adjust the size of the cap with respect to the patient's head. The opposing ends may include any suitable complementary securing structures (e.g., hook and loop fasteners, snap fasteners, etc.) to releasably secure the opposing ends of the outer structure layers together in an overlapped manner (e.g., similar in configuration to the overlapping layers of the thermal treatment garment described above and depicted in FIG. 3) during adjustment of the cap on the patient's head. In addition, any one or more of the other layers forming the cap may also be configured to overlap with each other in addition to the structure layers to enhance the adjustability of the cap to the patient's head.

The thermal treatment layer disposed within the thermal treatment cap can be of any suitable configuration and type, including the types described above for the previous embodiments, and is preferably disposed over substantially the entire gel layer. For example, as noted above, the thermal treatment layer can include any one or more heating devices including, without limitation, one or more etched foil silicon rubber heating pads, one or more thermoelectric devices (e.g., a Peltier chip) and/or any other thermal treatment devices that are disposed at selected locations within the thermal treatment layer and facilitate heating and/or cooling of the cap within desired temperature ranges.

Figure 7:
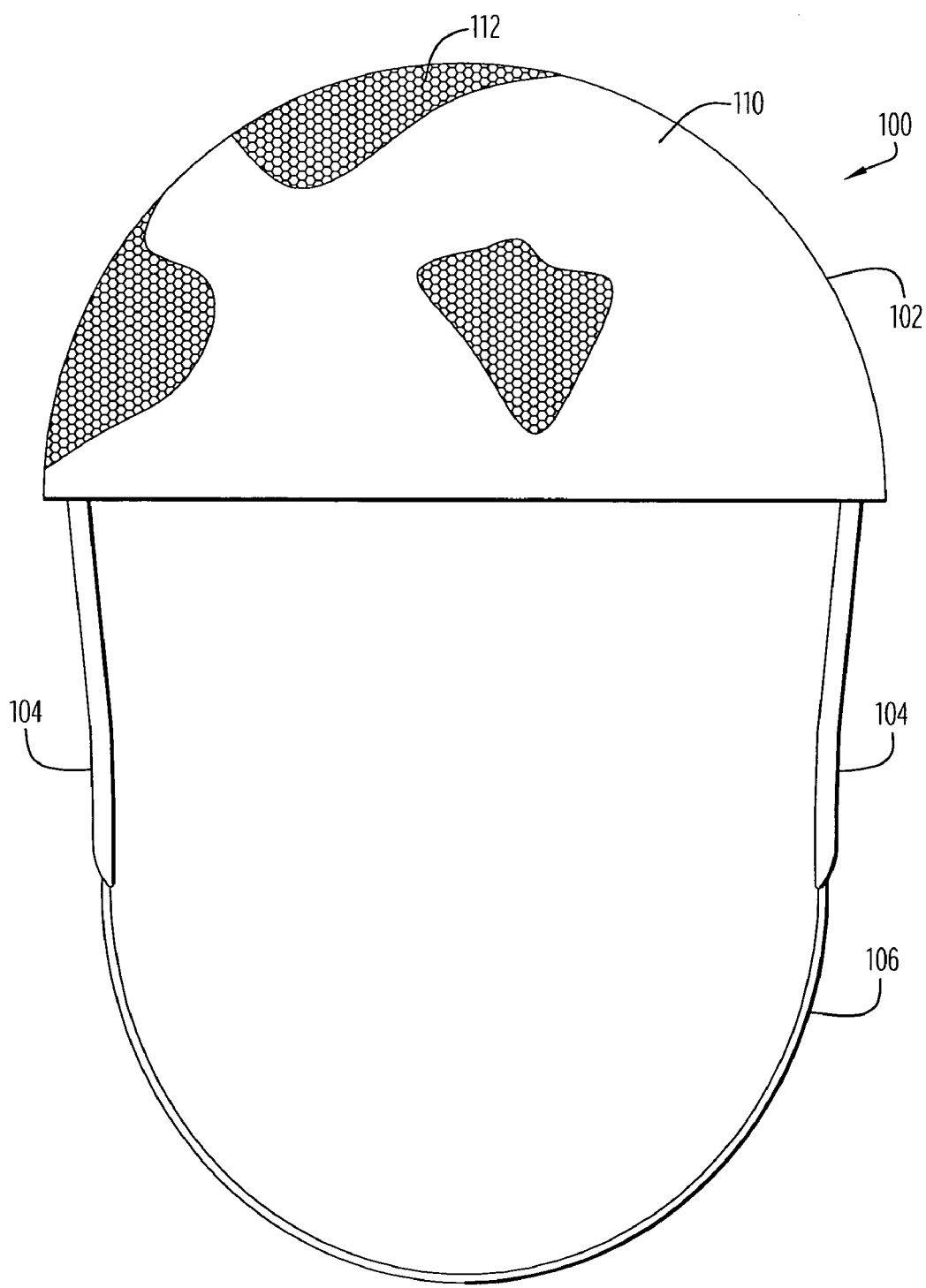
FIG. 7 is a front view in elevation of an adjustable thermal garment for covering portions of a human head in accordance with another embodiment of the present invention, where portions of an outer structure layer of the garment are removed to expose a thermal treatment layer.

In an exemplary embodiment as depicted in FIG. 7, the thermal treatment layer includes a metal wire grid or mesh that is disposed over the surface area of the gel layer. Portions of structure layer 110 have been removed in FIG. 7 so as to expose thermal treatment layer 112. The thermal treatment layer is constructed of a metal mesh that is adjacent and extends over substantially the entire surface area of the gel layer. The metal mesh is preferably constructed of a suitable metal material that has a sufficient thermal conductivity to ensure substantially uniform and even distribution of thermal energy from the mesh layer to the underlying gel layer during use of the cap.

Thermal treatment cap 102 further includes at least one temperature sensor (not shown) disposed within the cap at a suitable location proximate the thermal treatment layer, the gel layer and/or near a surface of the patient's head when the cap is worn to provide an accurate indication of the temperature at which the cap is thermally treating the head of the patient. The sensor(s) can be of any suitable type as described above (e.g., RTD, infrared, etc.) to provide a temperature indication to a controller for facilitating temperature control of the gel layer as described below.

Figure 8:
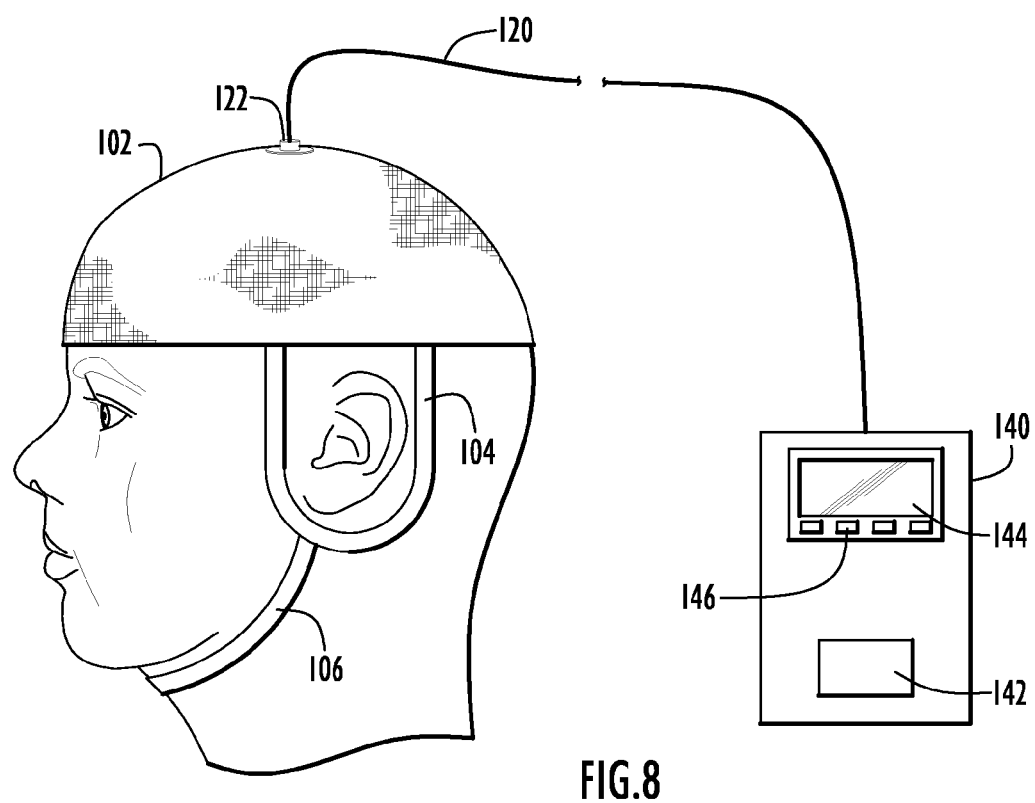
FIG. 8 is a view of a device in accordance with the present invention including a side view in elevation of the garment of FIG. 7 as worn by a user and a front view of a controller.

Referring to FIG. 8, thermal treatment cap 102 is connected with a controller 140 to facilitate temperature control of the gel layer within a desired temperature range. The thermal treatment cap includes a wiring sheath 120 extending from a cap opening 122 that extends through at least the structure layer and is disposed at an upper surface of the cap. The wiring sheath extends between the cap and controller 140 and includes wires that electrically couple or connect an electrical element of the thermal treatment layer and the temperature sensor(s) disposed within the cap to a processor 150 (FIG. 9) disposed within the controller. Optionally, the opening 122 in cap 102 includes a suitable swivel connection (as depicted in FIG. 8) that facilitates rotational and/or other movements of the cap with respect to the wiring sheath without disrupting the connections between the sensors, thermal treatment layer and wiring during use of the cap. The wiring sheath and corresponding wiring are optionally releasably securable, via suitable connection plugs and ports, to one or both of the thermal treatment cap and controller to facilitate selective connecting and disconnecting of the cap from one or more controllers in a particular medical application. Alternatively, the thermal treatment layer and sensor(s) may communicate with the controller via any suitable wireless connections (e.g., RF or IR communications).

Controller 140 may be implemented by any conventional or other microprocessor, controller and/or circuitry. The controller utilizes temperature indications from the sensors to control the heat transferred between the thermal treatment layer and the gel layer, which in turn maintains the thermal treatment cap within a desired temperature range. In particular, the controller controls power to the thermal treatment layer in a manner described below. The controller includes a power switch 142, a display 144 and controls or input devices 146. The controller may further be powered by any suitable power supply source (e.g., battery and/or power cord). The display may be implemented by any conventional or other display (e.g., LCD, LED, etc.) and displays measured temperatures, desired temperatures and/or other information (e.g., time, date, etc.). Input devices 146 (e.g., buttons, keys, etc.) enable entry of a desired temperature or temperature range and/or other information by a user to facilitate control of the display as well as the actual and/or set point temperatures at which the cap is to be thermally treated.

Optionally, the processor may record and selectively display a treatment time for the patient. The treatment time may be entered by an operator of the system via input devices 146. In addition, the controller may include any suitable audio and/or visual indicator to notify an operator of the system regarding when a selected treatment time is complete and/or if treatment temperatures fall outside of a preselected (e.g., user input) setpoint temperature range.

Figure 9:
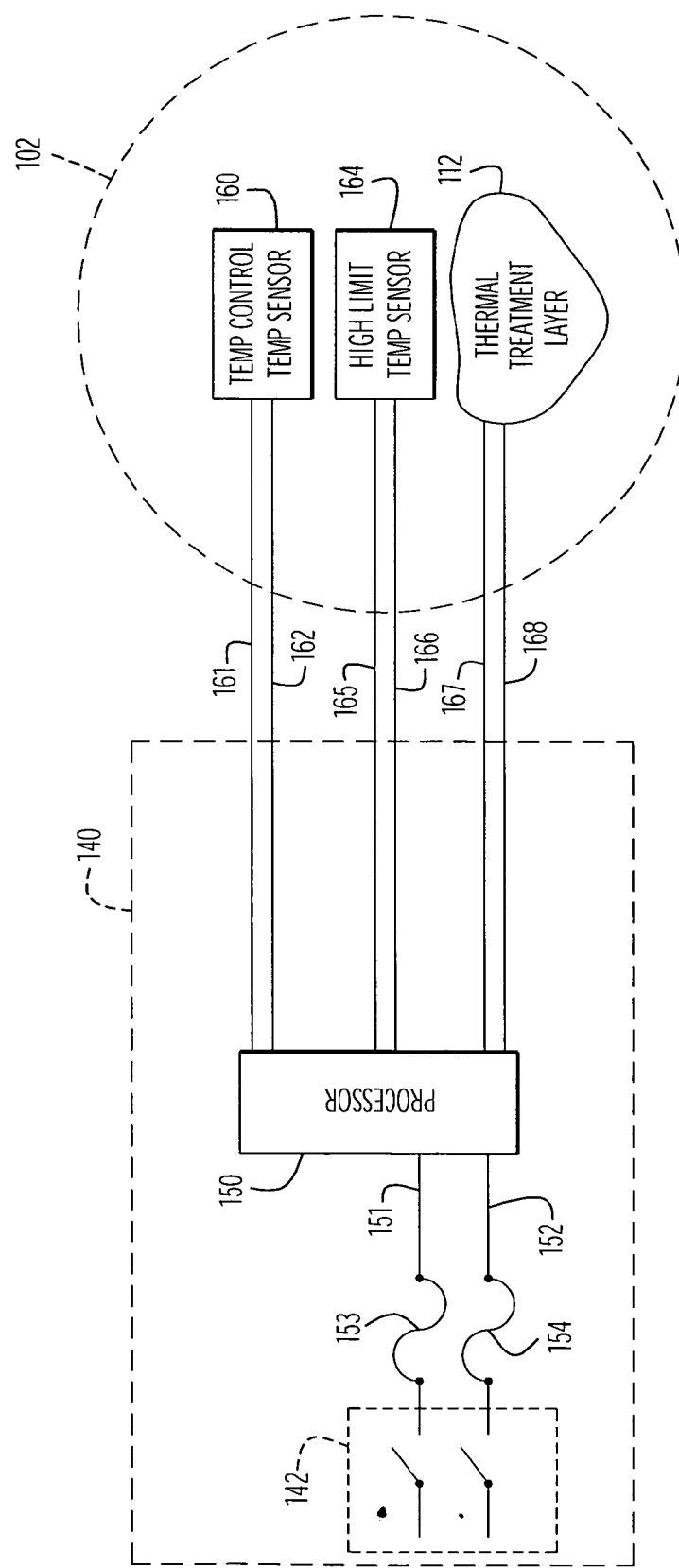
FIG. 9 is a schematic of an electric circuit for the garment of FIG. 7.

An exemplary schematic of an electrical circuit with which controller 140 controls the temperature of thermal treatment layer 112 is depicted in FIG. 9. Specifically, power switch 142 is connected via wires 151, 152 to a processor 150 within controller 140. The power switch is further connected to a supply source (not shown), such as a battery secured within the controller and/or via a power supply cord. Fuses 153, 154 are each connected in series with a respective wire 151, 152 to protect processor 150 in a conventional manner from any power surges from the power supply source. Processor 150 is also connected to a temperature sensor 160 disposed within the cap via wires 161, 162 and a high limit temperature sensor 164 disposed within the cap via wires 165, 166. In addition, the processor is connected to thermal treatment layer 112 of cap 102 via wires 167, 168. Wires 161, 162, 165, 166, 167, 168 are all disposed within wiring sheath 120 that extends between the controller and the thermal treatment cap.

Power is supplied to processor 150 by turning power switch 142 to an on position. A user can input a selected temperature or temperature range in which the cap is to be thermally treated by inputting the desired temperature information to processor 150 via input devices 146. The processor controls power supplied to thermal treatment layer 112 based upon the selected temperature or temperature range information input by the user, measured temperature information provided by temperature sensor 160 and/or measured temperature information provided by high limit temperature sensor 164. For example, in a heating application, if a temperature indication from temperature sensor 160 is equal to or exceeds a desired or user-specified temperature or temperature range, processor 150 disables power to thermal treatment layer 112. Alternatively, when a temperature indication from sensor 160 is less than the desired temperature, the processor enables power to the thermal treatment layer.

The processor further disables power to the thermal treatment layer when a temperature indication from high limit temperature sensor 164 exceeds a predetermined maximum allowable temperature. Power to the thermal treatment layer remains disabled until a temperature indication measured by the high limit temperature sensor is below the predetermined maximum allowable temperature.

During operation of the system of FIG. 8, peelable layer 116 is removed from gel layer 114 and thermal treatment cap 102 is placed on the head of a patient (and properly oriented such that straps 104 are secured around the patient's ears) such that the gel layer contacts selected portions of the patient's head. The cap is adjustably secured to the patient's head via chin strap 106. In embodiments where the thermal treatment cap removably separable from the controller, the cap is electrically coupled to the controller by securing the appropriate connections so that wiring sheath 120 extends between the cap and the controller. Power switch 142 is turned on to enable power to processor 150. The user may enter desired temperature information to the processor, via input devices 146. Alternatively, the processor may store previous temperature information corresponding with the patient and/or include default temperature information for controlling thermal treatments to the cap. The processor enables or disables power to thermal treatment layer 112 in the manner described above based upon measured temperature information provided by sensors 160 and 164. In addition, measured temperature information is displayed by the processor on display 144. Thermal treatment layer 112 provides substantially uniform and even thermal treatment to gel layer 114 disposed adjacent the thermal treatment layer, which in turn ensures substantially uniform thermal treatment to the portions of the patient's head in contact with the gel layer.

Figure 10:
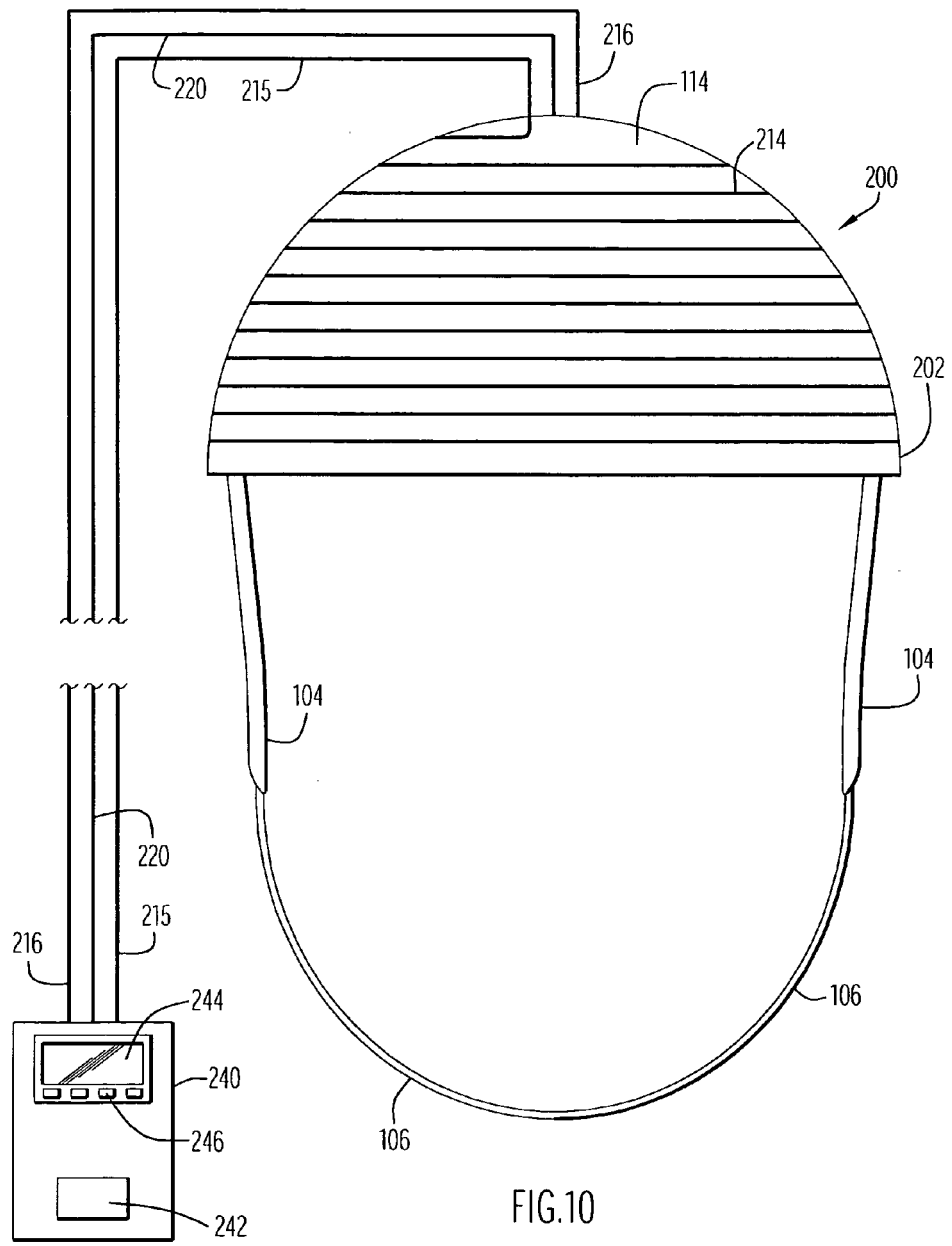
FIG. 10 is a view of a device in accordance with the present invention including a front view in elevation of a thermal cap with the structure layer of the cap removed to expose a thermal treatment layer and a front view of a controller.

An alternative embodiment in accordance with the present invention is depicted in FIG. 10 and includes a thermal treatment cap with a thermal treatment layer that utilizes fluid to thermally treat the cap and the head of the patient wearing the cap. Thermal treatment cap 202 of FIG. 10 includes structure, gel and peelable layers that are substantially similar to the thermal treatment cap described above and depicted in FIG. 9. However, the thermal treatment layer of cap 202 includes hollow tubing that surrounds the gel layer and is connected (or connectable) with a fluid supply source or reservoir to facilitate the flow of thermal treatment fluid through the tubing. The outer structure layer is removed from cap 202 of FIG. 10 in order to expose the tubing configuration that forms the thermal treatment layer. In particular, the thermal treatment layer of cap 202 includes tubing 214 that extends around the periphery of gel layer 112 in a spiraling manner to facilitate a substantially uniform distribution of heat transfer between the thermal treatment layer and the gel layer when thermal treatment fluid flows through the tubing. The tubing is preferably flexible and constructed of a suitable material (e.g., plastics such as polyvinyl chloride and/or other polymer materials).

Tubing 214 extends into a top portion of cap 202 (e.g., via an opening within the structure layer) from segment 215 so as to be disposed adjacent gel layer 112. The tubing extends in a spiraling manner around the periphery of the gel layer, increasing in distance from the top of the cap with each complete revolution about the periphery of the cap and with spacing between adjacent tubing revolutions being about the same. Upon reaching a lower surface portion of the cap, tubing 214 is directed upward so as to emerge at a segment 216 from the top portion of the cap (e.g., via the opening in the structure layer) at a location proximate the tubing inlet. Either tubing segment 215, 216 can serve as an inlet for fluid flow through the thermal treatment layer, depending upon the selection of fluid flow direction through the tubing, with the other tubing segment then serving as the outlet for fluid flow. However, the cap is not limited to the tubing configuration depicted in FIG. 10. Rather, any suitable tubing configuration can be utilized that is disposed proximate the gel layer and that preferably extends over a substantial portion of the gel layer so as to provide substantially uniform heat transfer between the gel layer and the thermal treatment layer.

Tubing segments 215 and 216 are connected to a fluid supply source or reservoir disposed, e.g., within controller 240 to facilitate the flow of a thermal treatment fluid from the fluid reservoir through tubing 214 during system operation. Optionally, either or both the cap and the fluid reservoir may include suitable connectors at their fluid inlet and outlet locations to facilitate a removable, fluid tight connection (e.g., via corresponding male and female threaded connectors) between the tubing within the cap and tubing segments extending between the cap and the controller. For example, providing tubing segments that are removably securable to one or both the cap and the fluid reservoir permits use of the cap with one or more different controllers and/or movement of the patient with respect to the fluid reservoir without the need for removing the cap from the patient's head.

Controller 240 is similar to the controller described above and depicted in FIG. 9, with the exception that the controller further includes the fluid reservoir, a thermal treatment device for thermally treating the fluid reservoir, and a pump for recirculating fluid from the fluid reservoir through the tubing during system operation. In particular, the controller includes a power switch 242, a display 244 and controls or input devices 246 that are substantially similar in configuration and function as the power switch, display and input devices of the controller of FIG. 9. The controller may further be powered by any suitable power supply source (e.g., battery and/or power cord).

The controller also includes a tank or reservoir (not shown) that includes a supply of a thermal treatment fluid, a pump 270 (FIG. 11) and a thermal treatment device 280 (FIG. 11) disposed proximate the reservoir to thermally treat the fluid stored within the reservoir for pumping through tubing 214. The fluid reservoir, thermal treatment source and/or pump may be disposed within the same housing of the controller or, alternatively, be disposed separate from the controller. The pump is connected to one of tubing segments 215, 216, while the reservoir is in fluid communication with the pump (e.g., via suitable tubing) and is further connected to the other of tubing segments 215, 216. In this configuration, the pump circulates fluid at a suitable flow rate between the reservoir and tubing 214. For example, the pump may be configured to draw fluid from the reservoir for delivery through tubing 214, where the fluid is then forced back to the reservoir for thermal treatment prior to recirculating of the fluid. Alternatively, the pump may be configured to force fluid from the reservoir through tubing 214, where the fluid then flows through the pump and back into the reservoir for thermal treatment prior to recirculating of the fluid.

The thermal treatment fluid can be any one or combinations of gaseous and/or liquid fluids (e.g., nitrogen, air, water, etc.) having a suitable thermal conductivity for providing thermal treatment to the cap within a desired temperature range as the fluid is forced through tubing 214 by the pump. In an exemplary embodiment, water is provided as thermal treatment fluid for the system of FIG. 10. In addition, the thermal treatment device is preferably any suitable device that can heat and/or cool the thermal treatment fluid to a temperature that is within a desired or user-specified range. An exemplary embodiment of a suitable thermal treatment device is a thermoelectric device (e.g., a heat pump or a Peltier chip) as described above that includes heat sinks coupled with the device to provide appropriate heating and/or cooling to the cap within a desired temperature range.

A wiring sheath 220 also extends from an opening (not shown) disposed in at least the structural layer in a top portion of cap 202 and includes wiring extending from temperature sensors disposed within the cap as described below. The wiring sheath houses the wiring and connects with cap 202 and controller 240 in a similar manner as the wiring sheath described above for the controller of FIG. 9. Further, a swivel connection can be provided at the connection of the wiring sheath with the cap to allow rotational and/or other movements of the cap with respect to the wiring sheath without disrupting connections between the wiring and components of the cap and controller during use of the cap. The wiring sheath and corresponding wiring are optionally releasably securable, via suitable connection plugs and ports, to either or both of the thermal treatment cap and the controller to facilitate connection of the cap with one or more different controllers depending upon a particular application. Alternatively, the temperature sensors of the cap may communicate with the processor of the controller via any suitable wireless connection (e.g., RF or IR communications).

Figure 11:
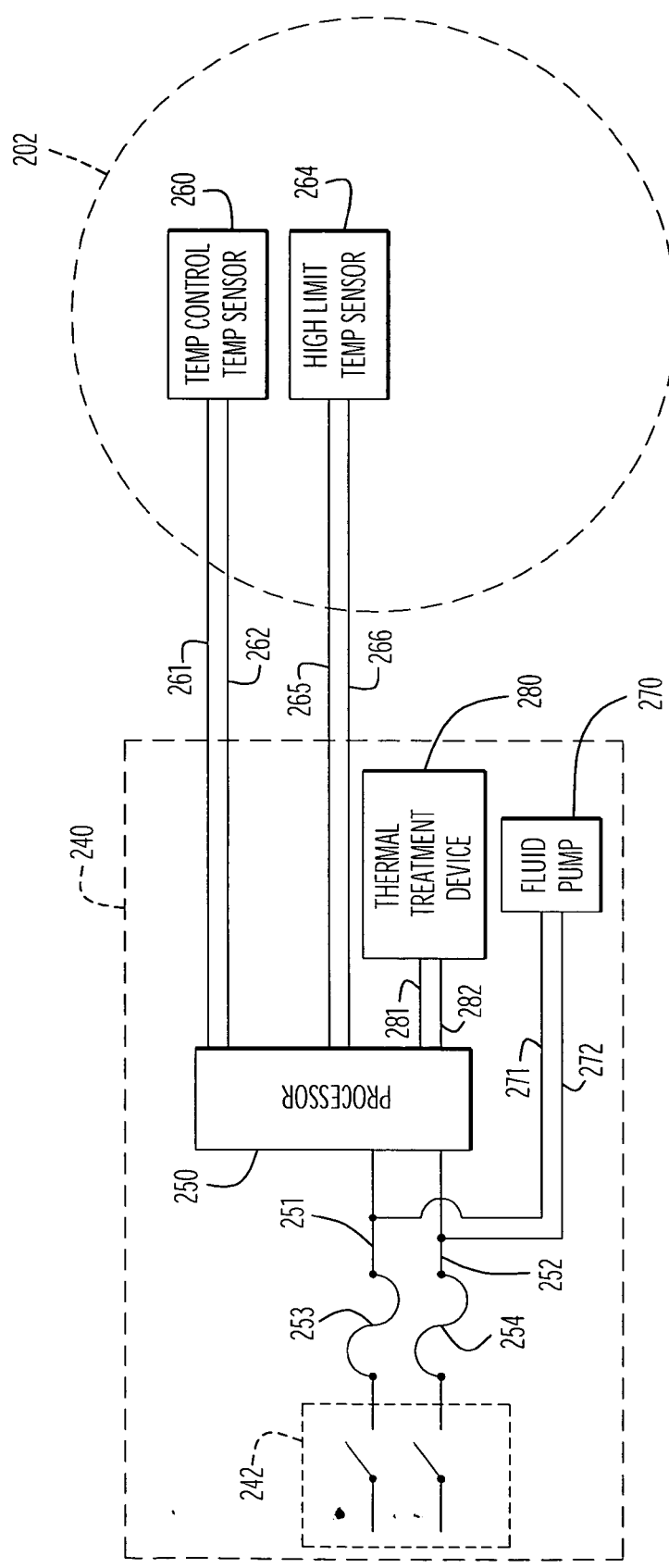
FIG. 11 is schematic of an electric circuit for the garment of FIG. 10.

An exemplary schematic of an electrical circuit with which controller 240 controls the temperature of the thermal treatment layer is depicted in FIG. 11. Specifically, power switch 242 is connected via wires 251, 252 to a processor 250 within controller 240. The power switch is further connected to a supply source (not shown), such as a battery secured within the controller and/or via a power supply cord. A pair of fuses 253, 254 are connected with wires 251, 252 to protect processor 250 in a conventional manner from any power surges from the power supply source. Processor 250 is also connected to a temperature sensor 260 via wires 261, 262 and a high limit temperature sensor 264 via wires 265, 266. Each of wires 261, 262, 265, 266 is disposed within the wiring sheath that extends between the controller and the thermal treatment cap. The processor is also connected with a fluid pump 270 via wires 271, 272 and a thermal treatment device 280 via wires 281, 282.

Power is supplied to processor 250 and pump 270 by turning power switch 242 to an on position. A user can input a selected temperature or temperature range in which the cap is to be thermally treated by inputting the desired temperature information to processor 250 via input devices 246. Upon enabling power to pump 270, the pump forces thermal treatment fluid from the reservoir through tubing 214, via tubing segments 215 and 216, and then back to the reservoir.

The processor controls power supplied to thermal treatment device 280 based upon the selected temperature or temperature range information input by the user, measured temperature information provided by temperature sensor 260 and/or measured temperature information provided by high limit temperature sensor 264. For example, in an embodiment where the thermal treatment device is a thermoelectric heat pump or Peltier chip, if a temperature indication from temperature sensor 260 is equal to or exceeds a desired or user-specified temperature or temperature range, processor 250 controls polarity and/or distribution of power to thermal treatment device 280 to facilitate cooling of the fluid in the reservoir via the appropriate heat sink(s). Alternatively, when a temperature indication from sensor 260 is less than the desired temperature, the processor controls polarity and/or distribution of power to the thermal treatment device to facilitate warming of the fluid within the reservoir via the appropriate heat sink(s). The controller can thus be configured to provide cooling to the cap by cooling the thermal treatment fluid within the reservoir to a preselected (e.g., user specified) temperature or temperature range. The controller can also be configured to provide heating to the cap by heating the thermal treatment fluid within the reservoir to a preselected temperature or temperature range. Further still, the controller can provide combined heating and cooling for a particular application to maintain the thermal treatment fluid at a precise temperature or within a narrow temperature range by cooling or warming the thermal treatment fluid depending upon measured temperature information provided by sensor 260.

The processor further disables power to the thermal treatment device when a temperature indication from high limit temperature sensor 264 exceeds a predetermined maximum allowable temperature. Power to the thermal treatment device remains disabled until a temperature indication measured by the high limit temperature sensor is below the predetermined maximum allowable temperature. This safety feature effectively prevents overheating of the cap by ceasing any heating of the thermal treatment fluid within the reservoir when the temperature measured by sensor 264 is greater than a maximum allowable value. Alternatively, or in addition to the high limit temperature sensor, the cap may also include a low limit temperature sensor that provides a temperature indication to the processor to disable power to the thermal treatment device to cease cooling of the thermal treatment fluid within the reservoir when the measured temperature drops below a predetermined minimum allowable temperature.

During operation of the system of FIG. 10, the peelable layer is removed from the gel layer and thermal treatment cap 202 is placed on the head of a patient (and properly oriented such that straps 104 are secured around the patient's ears) such that the gel layer contacts selected portions of the patient's head. The cap is adjustably secured to the patient's head via chin strap 106. Once the tubing segments 215, 216 and wiring in sheath 220 are appropriately secured between the cap and the controller, power switch 242 is turned on to enable power to processor 250 and pump 270. The user may enter desired temperature information to the processor, via input devices 246. Alternatively, the processor may store previous temperature information corresponding with the patient and/or include default temperature information for controlling thermal treatments to the cap.

Pump 270 circulates thermal treatment fluid through segments 215, 216 and tubing 214, and the processor enables or disables power to thermal treatment device 280 in the manner described above based upon measured temperature information provided by sensors 260 and 264. In addition, measured temperature information is displayed by the processor on display 244. The flow of thermal treatment fluid at controlled temperatures through tubing 214 provides substantially uniform and even thermal treatment to gel layer 114 disposed adjacent the tubing, which in turn ensures substantially uniform thermal treatment to the portions of the patient's head in contact with the gel layer.

In a modification to the embodiment of FIGS. 10 and 11, pump 270 may further be connected to processor 250 to facilitate control of different operational features of the pump by the processor. For example, the pump may include variable operational speeds to facilitate selective control of flow rates of fluid through the tubing in the thermal treatment cap. The processor may include programmable control features to control operation of the pump and flow rates of fluid through the tubing automatically and/or based upon inputs provided by the operator via input devices 246. In addition, the processor may be configured to disable both the thermal treatment device and the pump based upon measured temperature information from high limit temperature sensor 264.

While the embodiment employing a pump, tubing and thermal treatment fluid has been described above in relation to a thermal treatment cap, it is noted that this design can also be incorporated into each of the other thermal garment embodiments described above.

Each of the thermal garments described above can be further modified, in accordance with the present invention, to include any suitable thermal treatment material that effectively provides thermal treatment to the gel layer for heating and/or cooling of the user wearing the garment. For example, any of the thermal treatment garment embodiments described above can include a thermal treatment material (e.g., disposed within a thermal treatment layer and/or incorporated within the gel layer) comprising suitable phase change material that maintains the garment within a desired temperature range to effectively heat or cool the wearer of the garment. Phase change materials have very high latent heat capacities that result in absorbance or release of a significant amount of energy when these materials change between solid and liquid phases. In particular, a phase change material typically absorbs heat from its surroundings when the surrounding temperature is increased above its melting temperature (i.e., causing the phase change material to change from solid to liquid) and, conversely, releases heat to its surroundings when the surrounding temperature is decreased below its melting temperature (i.e., causing the phase change material to change from liquid to solid).

Phase change materials absorb and release substantially more energy per unit weight when changing between solid and liquid phase in comparison to the sensible heat absorbed or released by other (i.e., non-phase change) materials that are heated or cooled over the same temperature range. Thus, phase change materials are useful in providing thermal treatment in a variety of different applications and can be repeatedly converted between solid and liquid phases, or thermocycled, to absorb, store and release heat during such phase conversions.

Examples of phase change materials that can be used in the heat treatment layers of the present invention include organic compounds such as paraffin waxes and inorganic compounds such as hydrated salts. Examples of organic compounds that are useful as phase change materials include, without limitation, long, straight chain paraffinic hydrocarbons, typically in the range of $C_{10}$-$C_{44}$ carbon atoms, where the length of the carbon chain correlates with melting point of the compound (e.g., n-octacosane having a melting point of 61.4° C., and n-octadecane having a melting point of 28.2° C.). Other examples of organic phase change materials include, without limitation, polyethylene glycols (e.g., Carbowax 400 having a melting point of 4-8° C., Carbowax 1500 having a melting point of 44-48° C., and Carbowax 6000 having a melting point of 56-63° C.). Examples of inorganic compounds that are useful as phase change materials include, without limitation, hydrated salts such as calcium chloride hexahydrate ($CaCl_2 \cdot 6H_2O$) and magnesium nitrate hexahydrate ($Mg(NO_3)_2 \cdot 6H_2O$).

One or more phase change materials can be incorporated into the thermal treatment layer of any of the previously described thermal treatment garments of the invention (e.g., the thermal treatment cap of FIG. 6A). The phase change materials may be used alone or in combination with one or more of the previously described thermal treatment layer embodiments to achieve desired heating and/or cooling of the gel layer. In addition, the phase change materials may be incorporated directly within portions of the gel layer in addition to the thermal treatment layer. Further still, the thermal treatment layer may be eliminated altogether, and the phase change materials may be incorporated directly within portions of the gel layer to achieve a desired thermal treatment of the gel layer and garment.

One or more specific phase change materials can be selected for use in the thermal treatment layer based upon the melting points of the phase change materials and the desired temperature range at which the garment is to be maintained for a particular application. The garment including the thermal treatment layer with the selected phase change material(s) can then be thermally charged (e.g., heated or cooled) to a selected temperature to bring the garment including the phase change materials to a suitable temperature or within a suitable temperature range such that the phase change materials absorb a selected amount of thermal energy prior to use of the garment. The thermally charged thermal treatment layer including one or more phase change materials serves as an effective heat sink that provides a suitable heating and/or cooling treatment to the gel layer of the garment within a selected temperature range for an extended period of time. Upon completing a treatment application with the garment, the garment is again thermally charged to a suitable temperature or temperature range prior to a subsequent application of the garment.

It will be appreciated that the embodiments described above and illustrated in the drawings represent only a few of the many ways of implementing a thermal treatment garment and method of thermally treating body portions.

The garments described above may be applied to any portions of a human or animal body for any type of wound, bruise, sensitive area or for promotion of healing (e.g., burns, scars, skin disorders, muscle pulls, muscle strains, sprains, swelling or inflammation, circulatory problems, blood clots, etc.). The garments may be of any size or shape to accommodate any portions of bodies or any sized users. The garments can be formed to cover any portion of the body, including any one, combination, or portion of the following body parts: fingers, hands, wrists, elbows, shoulders, arms, the head, the scalp, the face and individual facial features, the neck, the torso, the back, the breasts, the waist, hips, the groin or genitals, legs, knees, ankles, feet, and toes. Thus, the garment of the present invention can be any one, portion or combination of the following garments or articles: a finger wrap, a glove, a mitt, head or wrist bands, a sleeve, a vest, a jacket or coat, shirt, sweater, a mask, a skull or head cap, a neck tube, a girdle, shorts, pants, leggings, a leg wrap, a sock, a toe wrap, scarf, undergarment, blanket (e.g., baby blanket, cover or quilt, etc.), bed sheet, etc. The vest may further include openings or garments for other body portions (e.g., sleeves, a neck portion, leg portions, etc.). The garments may include any quantity of panels of any shape or size fastened together at any suitable locations by any conventional or other fastening techniques or mechanisms (e.g., sewing, stitching, staples, heat fusing where the panels of the structure layer comprise an elastomeric or thermoplastic material, etc.). The garments may be of the pullover type, or be detachable at any locations to permit placement over body portions. The garments may include any quantity of any type of conventional or other fasteners (e.g., hook and loop fasteners, buckles, buttons, clasp or clipping mechanisms, snaps, straps with locking rings, zippers, string or fabric ties, straps or frictional force, etc.) disposed at any locations to secure the garment about a body portion. The edges of the garments and/or the garment layers (e.g., thermal treatment, structure, gel and/or intervening layers) may overlap or interleave in any fashion (e.g., individually or in any combination) and may be secured in any manner to facilitate placement of the garment over a body portion. In addition, the garments may be adjustable and, by way of example, include fasteners or straps that enable adjustment of the garment to accommodate various sized users or body portions.

The structure layer of the garments may include any quantity of layers of any suitable materials (e.g., nylon mesh, woven fabrics and textiles formed of natural and/or synthetic materials, non-woven fabrics and textiles formed of natural and/or synthetic materials, elastomeric materials, etc.). The intervening layer of the garments may include any quantity of layers of any suitable materials (e.g., a galvanized or ungalvanized elastomeric material or other material to which the gel layer may adhere, etc.). The protective layer of the garments may similarly include any quantity of layers of any suitable materials (e.g., plastic film, etc.). The structure, gel, thermal treatment, intervening and protective layers of the garments may be of any quantity, shape or size having any desired thickness and may be arranged in any desired fashion.

The gel layer of the garments may be disposed on any portions or quantity of portions of the structure, thermal and/or intervening layers. The gel layer may be disposed on the garments via any conventional or other fastening techniques (e.g., by the inherent self-adhesiveness of the gel material, pressure (e.g., pressing the layers together), heat, suitable adhesive, etc.). The gel layer can be bonded to the panels of the structure or other layers prior to securing the panels together, or the panels of the structure layer can be secured together prior to lining the garments with the gel and other layers. The gel layer of the garments may be secured to and detachable from any portion or portions of the structure, thermal treatment and intervening layers. The gel layer may include any quantity of segments of any shape or size disposed at any suitable locations within the garments. The gel layer may include any quantity of any additives (e.g., antimicrobial or other agents, medicaments, ointments, lotions, Aloe, Vitamin E or other vitamins, etc.), and may be implemented by a silicone gel, hydrogel, polyurethane gel or other suitable materials. The gel may further include any quantity and number of one or more phase change materials incorporated at selected locations within the gel layer to promote or enhance thermal treatment. The gel layer may have any degree of self-adhesiveness (e.g., including no or minimal self-adhesive properties). The gel layer preferably directly contacts the skin of a wearer, but may indirectly contact the wearer skin to thermally treat body portions (e.g., may contact wearer clothes or other articles, etc.). In addition, the gel layer may maintain a body portion relatively stationary with respect to the garment to prevent injury due to the body portion rubbing against the garment. For example, the gel layer of a garment in the form of a bra may maintain breast nipples (and/or the corresponding breasts) of a user (e.g., girl, woman, etc.) substantially stationary to prevent injury from rubbing (e.g., during walking, running, jogging, aerobics or any other activities).

The thermal treatment layer may be of any suitable type and quantity and may be disposed at any suitable locations on or within the garments (e.g., on any portions or quantity of portions of the structure, gel and/or intervening layers). The thermal treatment layer may be disposed on the garments and/or to any of the other layers (e.g., structure, gel and/or intervening layer) via any conventional or other fastening techniques (e.g., by the inherent self-adhesiveness of the gel material, pressure (e.g., pressing the layers together), heat, suitable adhesive, etc.). Alternatively, the thermal treatment layer may be incorporated into one or more different layers (e.g., within the gel layer). The thermal treatment layer of the garments may be secured to and detachable from any portion or portions of the structure, gel and intervening layers.

The thermal treatment layer may include any one or combination of different types of thermal elements to heat and/or cool the garment (e.g., heating pad, coils, wires, thermoelectric device, radiation, phase change materials, etc.). The thermal treatment layer may heat and/or cool the garment in any combination or fashion (e.g., heat, cool or heat and cool the garment). The thermal treatment layer may include any structure or housing to include the thermal element or the thermal element or layer may be embedded within other garment layers in any fashion. The thermal treatment layer may include any quantity of segments or units of any shape or size disposed at any suitable locations within the garments. The units may individually thermally treat the gel layer or wearer and each may be controlled by a corresponding or common controller (e.g., and temperature sensor) to the same or different temperature. The units may be detachable from the garment to enable thermal treatment of particular garment portions.

The controller may be implemented by any quantity of any conventional or other microprocessor, controller and/or circuitry and may control any quantity of thermal treatment layers or elements. The controller may control plural thermal treatment layers to the same or different temperatures, or a plurality of thermal treatment layers may each be controlled by a corresponding controller to the same or different temperatures. The controller may control the thermal treatment layer to any desired temperature or temperature range. By way of example only, the thermal treatment layer may be controlled to any temperature or range within about 20 degrees Fahrenheit to about 110 degrees Fahrenheit (about −6 degrees Celsius to about 44 degrees Celsius), and preferably within a body temperature range of about 86 degrees Fahrenheit to about 104 degrees Fahrenheit (about 30 degrees Celsius to about 40 degrees Celsius). The display may be implemented by any conventional or other display and display any desired information (e.g., set point temperature, actual temperature, time, date, etc.) in any scales or units. The power switch may be of any quantity, may be disposed at any location and may be implemented by any conventional or other switch (e.g., momentary, button, etc.). The input devices may be of any quantity, may be disposed at any locations and may be implemented by any conventional or other input devices (e.g., buttons, switches, keys, touch screen, etc.). The input devices may facilitate entry of any desired information (e.g., set point temperature, etc.). The controller may further maintain and display an elapsed time of thermal treatment when a garment is to be utilized for a prescribed time interval. The controller or garment may include an alarm (e.g., audio, visual, etc.) to indicate when a desired temperature or range is attained (or exceeded) or when a time interval expires. In embodiments employing a pump for pumping thermal treatment fluid (e.g., in the thermal treatment cap embodiment), the pump may be a variable or fixed flow rate pump, and the controller may further be configured to control enabling and disabling of the pump as well as pump speeds during system operations.

The temperature sensors may be of any quantity, may be disposed at any locations on or within the garment and may be implemented by any conventional or other temperature sensing device (e.g., RTD, infrared, etc.). The controller may control the thermal treatment layer in accordance with a preset or predetermined temperature or a user entered temperature or temperature range. The controller may utilize any quantity of user specified temperatures (e.g., maximum temperatures, minimum temperatures, etc.). Alternatively, the controller or other control device may be in the form of a power source to provide a safe power signal to the thermal treatment layer (e.g., without monitoring temperature or receiving temperature range information). The temperature sensors and thermal treatment layer may be coupled to the controller via any conventional or other communication medium (e.g., wire or cable, wireless transmission, etc.). The controller power source may be implemented by any type of conventional or other power source (e.g., batteries to enable transport, AC, DC, from a wall, vehicle or other outlet jack, etc.).

It is to be understood that the terms "left", "right", "front", "back", "rear", "top", "bottom", "upper", "lower", "horizontal", "vertical", "height", "length", "width", "thickness" and the like are used herein merely to describe points of reference and do not limit the present invention to any particular configuration or orientation.

From the foregoing description, it will be appreciated that the invention makes available a novel thermal treatment garment and method of thermally treating body portions, wherein a garment includes a thermal element to thermally treat garment gel material directly contacting the skin of a wearer.

Having described preferred embodiments of a new and improved thermal treatment garment and method of thermally treating body portions, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A thermal treatment device for thermally treating a portion of a user's body comprising:
    a cap to thermally treat the user's head and including:
        a structure layer;
        a gel layer coupled to the inner surface of the structure layer and forming an interior surface of the cap, wherein the interior surface of the gel layer is generally concave and contoured to engage with and at least partially envelop at least one selected portion of the user's head; and
        a thermal treatment layer coupled with the gel layer and configured to thermally treat the gel layer and the user;
        wherein one or more of said gel layer and thermal treatment layer are configurable to treat specific portions of said user's head and include a plurality of detachable sections each selectively removable from a corresponding layer to configure said one or more layers to cover and treat said specific portions of said user's head.

2. The device of claim 1, wherein said structure layer includes a generally convex outer surface with first and second overlapping sections and an inner surface that faces toward the user when the cap is worn by the user, wherein an amount of overlap between said first and second overlapping sections is selectively adjustable by the user to adjust a size of the cap to the user's head.

3. The device of claim 1, further comprising:
    a controller to control the thermal treatment layer to thermally treat the gel layer and the user to a selected temperature or within a selected temperature range.

4. The device of claim 3, wherein the controller includes an input device to facilitate entry of the selected temperature or selected temperature range and the controller controls the thermal treatment layer in accordance with the selected temperature or selected temperature range.

5. The device of claim 4, wherein the cap includes a temperature sensor to measure temperature of a portion of at least one of the cap and the user, wherein the controller controls the thermal treatment layer in accordance with the temperature measured by the temperature sensor.

6. The device of claim 5, wherein the controller includes a display to display at least one of the selected temperature or selected temperature range and the measured temperature.

7. The device of claim 5, wherein the cap further includes a high limit temperature sensor to measure temperature of a portion of at least one of the cap and the user, wherein the controller prevents the thermal treatment layer from thermally treating the gel layer when the measured temperature of the high limit temperature sensor exceeds a preselected maximum value.

8. The device of claim 3, wherein the thermal treatment layer of the cap includes a thermal element that is controlled by the controller to thermally treat the gel layer by at least one of heating the gel layer and cooling the gel layer.

9. The device of claim 8, wherein the thermal treatment layer of the cap includes an electrical heater to heat the gel layer.

10. The device of claim 9, wherein the electrical heater includes a wire mesh layer that engages a selected surface area portion of the gel layer.

11. The device of claim 1, wherein the thermal treatment layer comprises tubing that engages at least one portion of the gel layer, the tubing being configured to receive a flow of thermal treatment fluid that thermally treats the gel layer.

12. The device of claim 11, further comprising:
    a reservoir to store and supply the thermal treatment fluid to the tubing of the thermal treatment layer.

13. The device of claim 12, further comprising:
    a thermal element disposed proximate the reservoir; and
    a controller to thermally treat the thermal treatment fluid within the reservoir by at least one of heating the thermal treatment fluid and cooling the thermal treatment fluid.

14. The device of claim 12, further comprising:
    a pump connected between the reservoir and the tubing of the thermal treatment layer to facilitate recirculating of thermal treatment fluid between the reservoir and the tubing.

15. The device of claim 1, wherein the thermal treatment layer comprises a phase change material.

16. The device of claim 1, wherein the cap includes:
    at least one strap to secure the cap to the user's head by looping under the user's chin when the cap is worn by the user.

17. The device of claim 1, wherein the gel layer of the cap comprises one of a hydrogel gel and a polyurethane gel.

18. The device of claim 1, wherein the gel layer directly contacts portions of the user's head when the cap is worn by the user.

19. The device of claim 1, wherein the gel layer includes a medicament for application to the user's head.

20. A method of thermally treating a body portion via a cap including a structure layer, a gel layer coupled to the inner surface of said structure layer and forming a generally concave interior surface of the cap, and a thermal treatment layer coupled with the gel layer, the method comprising:
   (a) receiving a portion of the user's head within the cap such that the interior surface of the gel layer engages and at least partially envelops at least a selected portion of the user's head, wherein one or more of said gel layer and thermal treatment layer are configurable to treat specific portions of said user's head and include a plurality of detachable sections each selectively removable from a corresponding layer, and step (a) further includes:
      (a.1) selectively removing one or more of said detachable sections from a corresponding layer to configure said one or more layers to cover and treat said specific portions of said user's head;
   (b) applying thermal energy to the gel layer and the head portion received within the cap via the thermal treatment layer; and
   (c) controlling the application of the thermal energy from the thermal treatment layer to the gel layer and the head portion received in the cap.

21. The method of claim 20, wherein said structure layer includes a generally convex outer surface with first and second overlapping sections and an inner surface that faces toward a user, and step (a) further includes:
   (a.2) selectively adjusting an amount of overlap between said first and second overlapping sections to adjust a size of the cap to the user's head.

22. The method of claim 20, wherein step (c) further comprises:
   (c.1) controlling the thermal treatment layer via a controller to thermally treat the gel layer and the user to a selected temperature or within a selected temperature range.

23. The method of claim 22, wherein step (c.1) includes:
   (c.1.1) facilitating entry of the selected temperature or selected temperature range via an input device coupled with the controller.

24. The method of claim 22, wherein step (c.1) includes:
   (c.1.1) measuring a temperature of a portion of at least one of the cap and the user via at least one temperature sensor secured to the cap and coupled with the controller; and
   (c.1.2) controlling the thermal treatment layer via the controller based upon the temperature measured by the at least one temperature sensor.

25. The method of claim 22, further comprising:
   (d) displaying at least one of a measured temperature and the selected temperature or selected temperature range via a display coupled to the controller.

26. The method of claim 22, wherein the thermal treatment layer comprises an electrical heater.

27. The method of claim 26, wherein the electrical heater comprises a wire mesh layer that engages a selected surface portion of the gel layer.

28. The method of claim 20, wherein the thermal treatment layer comprises tubing that engages at least one portion of the gel layer, and step (b) includes:
   (b.1) flowing a thermal treatment fluid through the tubing to thermally treat the gel layer.

29. The method of claim 28, wherein step (b.1) includes:
   (b.1.1) circulating the thermal treatment fluid from a reservoir to and through the tubing via a pump.

30. The method of claim 29, wherein step (b.1) further includes:
   (b.1.2) thermally treating the thermal treatment fluid via a thermal element disposed proximate the reservoir.

31. The method of claim 20, wherein the thermal treatment layer comprises a phase change material, and step (c) includes:
   (c.1) thermally charging the phase change material prior to receiving the head portion within the cap.

32. The method of claim 20, wherein step (a) further includes:
   (a.2) securing the cap to the user's head by looping a strap connected to the cap under the user's chin.

* * * * *